United States Patent [19]
Bennett et al.

[11] Patent Number: 5,968,826
[45] Date of Patent: Oct. 19, 1999

[54] ANTISENSE INHIBITION OF INTEGRIN α4 EXPRESSION

[75] Inventors: C. Frank Bennett; Thomas P. Condon; Lex M. Cowsert, all of Carlsbad, Calif.

[73] Assignee: Isis Pharmaceuticals Inc., Carlsbad, Calif.

[21] Appl. No.: 09/166,203

[22] Filed: Oct. 5, 1998

[51] Int. Cl.$^6$ .............................. C07H 21/04; C12Q 1/68; C12N 15/00

[52] U.S. Cl. .............................. 435/375; 435/6; 435/91.1; 435/325; 435/366; 536/23.1; 536/24.31; 536/24.33; 536/24.5

[58] Field of Search ................................ 435/6, 91.1, 325, 435/366, 375; 514/44; 536/23.1, 24.3, 24.5, 24.33, 24.31

[56] References Cited

FOREIGN PATENT DOCUMENTS 0 688 784 A   9/1995   European Pat. Off. .

OTHER PUBLICATIONS

Lallier and Bronner–Fraser, "Inhibition of Neural Crest cell Attachment by Interin Antisense Oligonucleotides", Science, 1993, 259:692–695.

Kil, et al., "Inhibition of Cranial Neural Crest Adhesion in Vitro and Migration in Vivo Using Integrin Antisense Oligonucleotides", 1996, Devel. Biol. 179:91–101.

Breach TI BS 23:45–50, Feb. 1998.

Crooke, Ch 1 of Antisense Res. & Applications, Springer, 1998, pp. 1–50.

*Primary Examiner*—John LeGuyader
*Attorney, Agent, or Firm*—Law Offices of Jane Massey Licata

[57] ABSTRACT

Compositions and methods are provided for modulating the expression of integrin α4. Antisense compounds, particularly antisense oligonucleotides, targeted to nucleic acids encoding integrin α4 are preferred. Methods of using these compounds for modulating integrin α4 expression and for treatment of diseases associated with expression of integrin α4 are also provided.

11 Claims, No Drawings

# ANTISENSE INHIBITION OF INTEGRIN α4 EXPRESSION

FIELD OF THE INVENTION

The present invention provides compositions and methods for modulating the expression of integrin α4. In particular, this invention relates to antisense compounds, particularly oligonucleotides, specifically hybridizable with nucleic acids encoding human integrin α4. Such oligonucleotides have been shown to modulate the expression of human integrin α4.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature (Harlan, J. M., Blood 1985, 65, 513–525). This response is mediated by the interaction of adhesion molecules expressed on the cell surface of leukocytes and vascular endothelial cells. Very late antigen-4 (also called VLA-4, α4β1 or CD49d/CD29) is a homodimeric adhesion receptor which is composed of noncovalently linked α and β subunits and serves to mediate leukocyte adhesion to vascular cell adhesion molecule-1 (VCAM-1) which is expressed on cytokine-stimulated endothelial cells. This interaction between VCAM-1 and VLA-4 contributes to leukocyte extravasation in acute and chronic inflammatory conditions including multiple sclerosis (MS), rheumatoid arthritis, asthma, psoriasis and allergy.

Fibronectin is also a ligand for VLA-4. Fibronectin plays an important role in many processes including embryonic development, wound healing and tumor cell metastasis (Guan, J.-L. and Hynes, R. O., Cell 1990, 60, 53–61).

VLA-4 is a heterodimer of an α4 integrin and β1 integrin. The α4 integrin can also heterodimerize with a β7 integrin chain to form integrin α4β7 which is known as a mucosal homing receptor because its primary ligand is the mucosal vascular addressing MadCAM-1. Integrin α4β7 identifies a subset of memory T cells with a tropism for the intestinal tract, whereas integrin α4β1 (VLA-4) is constitutively expressed on most mononuclear leukocytes, but not on circulating neutrophils. The interaction of VCAM-1 with VLA-4 suggests that VLA-4 is a potential therapeutic target for inflammatory diseases, including atherosclerosis, allergy and asthma, arthritis, and tumor cell metastasis (Kassner, P. D., et al, Adv. Exp. Med. Biol. 1992, 323, 163–170). VLA-4 has also been found to play a role in promoting adhesion (i.e., retention) of hemopoietic stem cells in the bone marrow (Papayannopoulou and Nakamoto, Proc. Natl. Acad. Sci. U.S.A. 1993, 90, 9374–9378).

Asthma is an inflammatory disease associated with eosinophil infiltration into the lung. VLA-4 is expressed on eosinophils. Metzger, W. J. (Springer Semin. Immunopathol. 1995, 16, 467–478) used a rabbit model of asthma to demonstrate that both an anti-VLA-4 antibody and a CS-1 peptide could reduce eosinophil infiltration into the lung and reduce the development of asthma.

Rheumatoid arthritis is another disease associated with inflammation. Muller-Ladner, U., et al., (J. Rheumatology 1997, 24, 1873–1880) found that the alternatively spliced form of fibronectin containing CS-1 was expressed in the rheumatoid synovium. Additionally, they found that not only did expression of fibronectin result in recruitment of VLA-4 expressing cells, but fibroblasts in the rheumatoid synovium expressed VLA-4. Seiffge, D. (J. Rheumotology 1996, 23, 2086–2091) used a rat model for arthritis to show that a monoclonal antibody to the α4 chain of VLA-4 resulted in an improvement of symptoms.

VLA-4 also plays a role in a number of autoimmune diseases. Marazuela, M., et al., (Eur. J. Immunol. 1994, 24, 2483–2490) found elevated expression of both the VLA-4/VCAM-1 and LFA-1/ICAM-1,3 pathways in Graves' disease and Hashimoto's thyroiditis, suggesting that both play a role in these diseases. VLA-4 may also play a role in multiple sclerosis. Antibodies to VLA-4 have been found to prevent experimental autoimmune encephalomyelitis (EAE), an experimentally induced disease with similarities to multiple sclerosis (Yednock, T. A., et al., Nature 1992, 356, 63–66). Elevated expression levels of VLA-4 were detected in a patient with systemic lupus erythematosus (Takeuchi, T., et al., Clin. Rheumatology 1995, 14, 370–374). VLA-4 is involved in cellular responses to two surgical procedures, transplantation and vascular reconstructive procedures. Allograft rejection is a common response to transplantation of a foreign tissue. CS-1 peptides have been found to prevent both acute rejection (Coito, A. J., et al., Transplantation 1998, 65, 699–706) and chronic rejection (Korom, S., et al., Transplantation 1998, 65, 854–859) by blocking VLA-4 binding to fibronectin. During vascular reconstructive surgery, a common cause of failure is intimal hyperplasia which results from the accumulation of monocytes and lymphocytes. In a baboon model, Lumsden, A. B., et al.,(J. Vasc. Surg. 1997, 26, 87–93) demonstrated that an anti-VLA-4 antibody reduced intimal hyperplasia.

VLA-4 also plays a role in tumor cell metastasis. In metastasis, tumor cells must cross the extracellular matrix, enter the circulatory system and invade into new tissue. Bao, L. et al., (Differentiation 1993, 52, 239–246) detected VLA-4 expression of many human tumor cell lines, including a breast carcinoma, melanoma, and renal carcinoma, and found that the presence of VLA-4 correlated well with metastatic potential. Kawaguchi, S. et al., (Jpn. J. Cancer Res. 1992, 83, 1304–1316) transfected a cDNA encoding the α4 subunit of VLA-4 into a human fibrosarcoma cell line. These cells overexpressed VLA-4 and showed increased in vitro invasive ability. Augmentation of metastasis by IL-1 (Garofalo, A.,et al., Cancer Res. 1995, 55, 414–419) or TNF-α (Okahara, H., et al., Cancer Res. 1994, 54, 3233–3236) has been shown to involve the interaction between VLA-4 and VCAM-1. These authors suggest that a therapy directed towards inhibiting this interaction would be useful in reducing the risk of metastasis with conditions associated with high serum concentrations of TNF-α, including cachexia, sepsis, surgical stress, or TNF-α therapeutic applications. Because tumor cells often secrete IL-1 and TNF-α, such a therapy may be useful in reducing the risk of metastasis associated with such tumor cells.

VLA-4 is involved in promoting retention of hemopoietic progenitor cells in the bone marrow. Antibodies to integrin α4 (but not integrin β2) have been found to selectively mobilize progenitor/stem cells into the bloodstream (Papayannopoulou and Nakamoto, *Proc. Natl. Acad. Sci. U.S.A.* 1993, 90, 9374–9378). This mobilization is of clinical relevance in the field of bone marrow transplantation as it obviates the need for marrow harvesting by making hemopoietic progenitor cells available in the circulating blood.

While steroids and other antiinflammatory drugs are effective in treating inflammatory diseases and conditions, long-term usage often leads to side effects such as increased risk of infection caused by impairment of phagocytic leukocyte migration and function. There is some concern that inhibition of the function of the β1 integrin chain may be associated with increased susceptibility to infections, as demonstrated by a β1 (also called CD18) monoclonal antibody in rabbits (Foster, C. A., 1996, *J. Allergy Clin. Immunol.*, 98, 270–277). It is believed that selective inhibition of the α4 chain may be a more desirable approach. Inhibition of the α4 chain is believed likely to reduce levels of the VLA-4 heterodimer as well as the α4β7 heterodimer.

Potential therapeutic interventions targeting VLA-4 include monoclonal antibodies, and peptide antagonists. Leger, O. J. P., et al. (*Human Antibodies* 1997, 8, 3–16) describe a monoclonal antibody against VLA-4 that is in phase II clinical trials for multiple sclerosis. CS-1 peptide antagonists have been described by Jackson, D. Y., et al. (*J. Med. Chem.* 1997, 40, 3359–3369).

Hayashi et al. (*Cell Struct. Funct.* 1991, 16, 241–249) have used a vector expressing RNA complementary to chicken integrin β1 to reduce integrin β1 expression, resulting in altered cell attachment and shape.

Antisense oligonucleotides targeted to various integrins have been used as tools to dissect the functional interactions of integrins in complex settings. Lallier and Bronner-Fraser (*Science*, 1993, 259, 692–695) have used phosphorothioate oligonucleotides targeted to conserved and nonconserved regions of chick β1, human α4, rat α1 and human α5 integrins to determine the effects of these integrins on cell attachment. These same oligonucleotides were also injected into cranial neural crest migratory pathways in avian embryos, and it was demonstrated that those oligonucleotides that inhibited cell attachment in vitro also caused neural crest and/or neural tube abnormalities in vivo (Kil et al., *Devel. Biol.* 1996, 179,91–101).

EP patent application 688 784 (Carolus et al.) discloses 3' derivatized oligonucleotide analogs, including one sequence targeted to the β1 subunit of VLA-4.

Antisense oligonucleotides are believed to represent a useful means of modulating the expression of integrin α4 and of treating diseases associated with its expression.

SUMMARY OF THE INVENTION

The present invention is directed to antisense compounds, particularly oligonucleotides, which are targeted to a nucleic acid encoding integrin α4, and which modulate the expression of integrin α4. Pharmaceutical and other compositions comprising the antisense compounds of the invention are also provided. Further provided are methods of modulating the expression of integrin α4 in cells or tissues comprising contacting said cells or tissues with one or more of the antisense compounds or compositions of the invention. Further provided are methods of treating an animal, particularly a human, suspected of having or being prone to a disease or condition associated with expression of integrin α4 by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding integrin α4, ultimately modulating the amount of integrin α4 produced. This is accomplished by providing antisense compounds which specifically hybridize with one or more nucleic acids encoding integrin α4. As used herein, the terms "target nucleic acid" and "nucleic acid encoding integrin α4" encompass DNA encoding integrin α4, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of integrin α4. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding integrin α4. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding integrin α4, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$—[ wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2- methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. patent application Ser. No. 09/016,520, filed on Jan. 30, 1998, which is commonly owned with the instant application and the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference and allowed U.S. patent application Ser. No. 08/468,037, filed on Jun. 5, 1995, which is commonly owned with the instant application and is also herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, Kroschwitz, J. I., ed. John Wiley & Sons, 1990, 858–859 those disclosed by Englisch et al., (*Angewandte Chemie, IE,* 1991, 30, 613), and those disclosed by Sanghvi, Y. S., (*Antisense Research and Applications*, 15,289–302), and Crooke, S. T. and Lebleu, B., ed., (*CRC Press,* 1993). Certain of these nucleobases are particularly useful for increasing the binding affinity of the oligomeric compounds of the invention. These include 5-substituted pyrimidines, 6-azapyrimidines and N-2, N-6 and O6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 59, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937).

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599, 928; and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference, and allowed U.S. patent application Ser. No. 08/465,880, filed on Jun. 6, 1995, which is commonly owned with the instant application and also herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al. *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of integrin α4 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding integrin α4, enabling sandwich and other assays to easily be constructed to exploit this fact. Hybridization of the antisense oligonucleotides of the invention with a nucleic acid encoding integrin α4 can be detected by means known in the art. Such means may include conjugation of an enzyme to the oligonucleotide, radiolabelling of the oligonucleotide or any other suitable detection means. Kits using such detection means for detecting the level of integrin α4 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33). One or more penetration enhancers from one or more of these broad categories may be included. Penetration enhancers are described in pending U.S. patent application Ser. No. 08/886,829, filed on Jul. 1, 1997, and pending U.S. patent application Ser. No. 08/961,469, filed on Oct. 31, 1997, both of which are commonly owned with the instant application and both of which are herein incorporated by reference.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33; El-Hariri et al., *J. Pharm. Pharmacol.*, 1992, 44, 651–654). Examples of some presently preferred fatty acids are sodium caprate and sodium laurate, used singly or in combination at concentrations of 0.5 to 5%.

Preferred penetration enhancers are disclosed in pending U.S. patent application Ser. No. 08/886,829, filed on Jul. 1, 1997, which is commonly owned with the instant application and which is herein incorporated by reference.

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y. 1996, pages 934–935). Various natural bile salts, and their synthetic derivatives, act as penetration enhancers. Thus, the term "bile salt" includes any of the naturally occurring components of bile as well as any of their synthetic derivatives. Preferred bile salts are described in pending U.S. patent application Ser. No. 08/886,829, filed on Jul. 1, 1997, which is commonly owned with the instant application and which is herein incorporated by reference. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, 8, 92–192; Muranishi, *Critical Reviews in Therapeutic Drug Carrier Systems*, 1990, 7, 1–33; Buur et al., *J. Control Rel.*, 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, 8, 92–191); and perfluorochemical emulsions, such as FC-43 (Takahashi et al., *J. Pharm. Pharmacol.*, 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, 8, 92–191); and non-steroidal anti-inflammatory agents such as diclofenac sodium, indomethacin and phenylbutazone (Yamashita et al., *J. Pharm. Pharmacol.*, 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698–708).

Liposome preparation is described in pending U.S. patent application Ser. No. 08/961,469, filed on Oct. 31, 1997, which is commonly owned with the instant application and which is herein incorporated by reference.

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 1987, Berkow et al., eds., Rahway, N.J., 1206–1228. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 1987, Berkow et al., eds., Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1
Nucleoside Phosphoramidites for Oligonucleotide Synthesis
Deoxy and 2'-alkoxy Amidites 2'-Deoxy and 2'-methoxy beta-cyanoethyldiisopropyl phosphoramidites are purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides is utilized, except the wait step after pulse delivery of tetrazole and base is increased to 360 seconds.

Oligonucleotides containing 5-methyl-2'-deoxycytidine (5-Me-C) nucleotides are synthesized according to published methods (Sanghvi, et. al., *Nucleic Acids Research*, 1993, 21, 3197–3203) using commercially available phosphoramidites (Glen Research, Sterling, Va. or ChemGenes, Needham, Mass.).
2'-Fluoro Amidites
  2'-Fluorodeoxyadenosine Amidites
  2'-fluoro oligonucleotides are synthesized as described previously (Kawasaki, et. al., *J. Med. Chem.*, 1993, 36, 831–841) and U.S. Pat. No. 5,670,633, herein incorporated by reference. Briefly, the protected nucleoside N6-benzoyl-2' deoxy-2'-fluoroadenosine is synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine is selectively protected in moderate yield as the 3',5'-ditetrahydropyranyl (THP) intermediate. Deprotection of the THP and N6-benzoyl groups is accomplished using standard methodologies and standard methods are used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine is accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

2'-Fluorouridine

Synthesis of 2'-deoxy-2'-fluorouridine is accomplished by the modification of a literature procedure in which 2,2'-anhydro- 1-beta-D-arabinofuranosyluracil is treated with 70% hydrogen fluoride-pyridine. Standard procedures are used to obtain the 5'-DMT and 5'-DMT-3'phosphoramidites.

2'-Fluorodeoxycytidine

2'-deoxy-2'-fluorocytidine is synthesized via amination of 2'-deoxy-2'-fluorouridine, followed by selective protection to give N4-benzoyl-2'-deoxy-2'-fluorocytidine. Standard procedures are used to obtain the 5'-DMT and 5'-DMT-3'phosphoramidites.

2'-O-(2-Methoxyethyl) Modified Amidites

2'-O-Methoxyethyl-substituted nucleoside amidites were prepared as follows, or alternatively, as per the methods of Martin, P., (*Helvetica Chimica Acta*, 1995, 78, 486–504).

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/Acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxytetra (isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/Hexane (3:1) as the eluting solvent. The pure fractions were combined to give 90.6 g (87%) of the title compound.

2'-(Aminooxyethyl)nucleoside amidites and 2'-(dimethylaminooxyethyl)nucleoside amidites Aminooxyethyl and dimethylaminooxyethyl amidites are prepared as per the methods of U.S. patent application Ser. No. 10/037,143, filed Feb. 14, 1998, and Ser. No. 09/016,520, filed Jan. 30, 1998, each of which is commonly owned with the instant application and is herein incorporated by reference.

Example 2

Oligonucleotide synthesis

Unsubstituted and substituted phosphodiester (P=O) oligonucleotides were synthesized on an automated DNA synthesizer (Applied Biosystems model 380B) using standard phosphoramidite chemistry with oxidation by iodine.

Phosphorothioates (P=S) were synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. No. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)]Chimeric Phosphorothioate Oligonucleotides

[2'-O-(2-methoxyethyl)]--[2'-deoxy]--[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl)Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162–18171). Results obtained with HPLC-purified material are similar to those obtained with non-HPLC purified material.

Example 7
Analysis of Oligonucleotide Inhibition of Integrin α4 Expression

Antisense modulation of integrin α4 expression can be assayed in a variety of ways known in the art. For example, integrin α4 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al. (*Current Protocols in Molecular Biology,* 1993., 1, 4.1.1–4.2.9 and 4.5.1–4.5.3). Northern blot analysis is routine in the art and is taught in, for example, Ausubel, F. M. et al. (*Current Protocols in Molecular Biology* 1996, 1, 4.2.1–4.2.9). Real-time quantitative (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

Integrin α4 protein levels can be quantitated in a variety of ways well known in the art, such as immunoprecipitation, Western blot analysis (immunoblotting), ELISA or fluorescence-activated cell sorting (FACS). Antibodies directed to integrin α4 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al. (*Current Protocols in Molecular Biology* 1997, 2, 11.12.1–11.12.9). Preparation of monoclonal antibodies is taught in, for example, Ausubel, F. M. et al. (*Current Protocols in Molecular Biology* 1997, 2, 11.4.1–11.11.5).

Immunoprecipitation methods are standard in the art and can be found at, for example, Ausubel, F. M. et al. (*Current Protocols in Molecular Biology* 1998, 2, 10.16.1–10.16.11). Western blot (immunoblot) analysis is standard in the art and can be found at, for example, Ausubel, F. M. et al. (*Current Protocols in Molecular Biology* 1997, 2, 10.8.1–10.8.21). Enzyme-linked immunosorbent assays (ELISA) are standard in the art and can be found at, for example, Ausubel, F. M. et al. (*Current Protocols in Molecular Biology* 1991, 2, 11.2.1–11.2.22).

Example 8
Antisense Inhibition of Human Integrin α4 Expression

In accordance with the present invention, a series of oligonucleotides were designed to target different regions of the human integrin α4 RNA, using published sequences (GenBank accession number L12002, incorporated herein as SEQ ID NO: 1). The oligonucleotides are shown in Table 1. Target sites are indicated by nucleotide numbers, as given in the sequence source reference (GenBank accession no. L12002), to which the oligonucleotide binds. All compounds in Table 1 are 18 nucleotides in length, with a phosphorothioate backbone and a centered 10-base deoxynucleotide gap flanked by 2'-methoxyethoxy (2'MOE) wings. Human A375 melanoma cells (American Type Culture Collection, Manassas, Va.) were plated at 2000 cells/cm² two days before oligonucleotide treatment. Cells were treated with oligonucleotides at a dose of 200 nM oligonucleotide and 6 ug/ml LIPOFECTIN for four hours. Cells were incubated overnight and harvested with 2 mM EDTA in PBS. Cells were washed in 2% bovine serum albumin, 0.2% sodium azide in D-PBS at 4° C. Cells were centrifuged at 200×g, and the supernatant was decanted. Protein levels were determined by flow cytometry according to published methods (Condon and Bennett, *J. Biol. Chem.* 1996, 271, 30398–30403). The specific conjugated antibody CD49d-FITC (Immunotech, Westbrook, Me., clone HP2/1) was added at 2 uL/test well, and the control IgG (mouse IgG1-FITC, PharMingen, San Diego, Calif.) was added at a concentration of ug/mL. Antibodies were incubated with the cells for 30 minutes at 4° C. in the dark, under gentle agitation. Cells were washed again as above and then resuspended in 0.3 ml of FacsFlow buffer with 0.5% formaldehyde. Cells were analyzed on Becton Dickinson FAC-Scan. Results are expressed as percentage of control expression based on mean fluorescence intensity.

As shown in Table 1, oligonucleotides 24453, 24473, 24475, 24477 and 24451 gave at least about 50% inhibition of integrin α4 protein expression and were subjected to further study.

Example 9
Dose Response Curves for Effect of Antisense Oligonucleotides on Integrin α4 Protein Expression A375 cells were treated with ISIS 24473, 24475, 24477 and 24451 at concentrations of 50, 100, 200 and 400 nM for 4 hours. Cells were harvested with trypsin at 48 and 72 hours after oligonucleotide treatment and stained with 2 ug/ml CD49d-FITC as in the previous example. Results are shown in Table 2.

TABLE 1

Inhibition of human integrin α4 protein levels by antisense oligonucleotides

| ISIS # | Sequence | Target region | Target site | % Control | % Inhib | SEQ ID NO |
|---|---|---|---|---|---|---|
| 24439 | CTCCGTCTCTGCCTACGC | 5'-UTR | 0087-0104 | 120 | — | 2 |
| 24440 | CGGGTGCTCGCGCTGCTT | 5'-UTR | 0163-0180 | 101 | — | 3 |
| 24441 | CCTGGGATGCCGCGCACT | 5'-UTR | 0224-0241 | 112 | — | 4 |

TABLE 1-continued

Inhibition of human integrin α4 protein
levels by antisense oligonucleotides

| ISIS # | Sequence | Target region | Target site | % Control | % Inhib | SEQ ID NO |
|---|---|---|---|---|---|---|
| 24442 | ATGAGGCGCAGCGTGTCC | 5'-UTR | 0318-0335 | 82 | 18 | 5 |
| 24443 | CAAAGTTGCACGGGATGC | 5'-UTR | 0370-0387 | 63 | 37 | 6 |
| 24444 | GGAACATTCAACACTAAG | AUG | 0400-0417 | 68 | 32 | 7 |
| 24445 | CCCGGGTTCGCGCCTCGC | coding | 0443-0460 | 73 | 27 | 8 |
| 24446 | GCGCGCTCTCAGTGTCCA | coding | 0535-0552 | 58 | 42 | 9 |
| 24447 | GTGGCTGTGCAGCACGAC | coding | 0594-0611 | 76 | 24 | 10 |
| 24448 | ACTGAAGCGTTGGCGAGC | coding | 0656-0673 | 55 | 45 | 11 |
| 24449 | GCACGTCTGGCCGGGATT | coding | 0714-0731 | 61 | 39 | 12 |
| 24451 | CCACTGATTGTCTCTCTC | coding | 0789-0806 | 51 | 49 | 13 |
| 24452 | GGATCCATTTTCTCCTGG | coding | 0831-0848 | 60 | 40 | 14 |
| 24453 | GCTTATTTTCATTCTTTA | coding | 0889-0906 | 47 | 53 | 15 |
| 24454 | TTCTTTTACTCAGTTCTG | coding | 0949-0966 | 53 | 47 | 16 |
| 24455 | TCACATAATCTTGATAAC | coding | 0976-0993 | 81 | 19 | 17 |
| 24456 | CCCATCACAATTAAATCC | coding | 1052-1069 | 76 | 24 | 18 |
| 24457 | TTATTTGTAGTTATATTG | coding | 1112-1129 | 106 | — | 19 |
| 24458 | CCTAAATAACTTCCAAAT | coding | 1166-1183 | 88 | 12 | 20 |
| 24459 | GAAAATGACCAGCTCCGA | coding | 1192-1209 | 61 | 39 | 21 |
| 24460 | TTTCATGTAAGATATTTA | coding | 1300-1317 | 94 | 06 | 22 |
| 24461 | CCACAGCACAGACAGAAG | coding | 1351-1368 | 69 | 31 | 23 |
| 24462 | TGGTGCTCTGCATGGGTG | coding | 1408-1425 | 65 | 35 | 24 |
| 24463 | TACACAAACACTCTTCCT | coding | 1436-1453 | 101 | — | 25 |
| 24464 | TTTGTTTCCATTGCATTC | coding | 1481-1498 | 62 | 38 | 26 |
| 24465 | TGCAGCATATTTGTCACT | coding | 1509-1526 | 63 | 37 | 27 |
| 24466 | TTGTCAATGTCGCCAAGA | coding | 1550-1567 | 64 | 36 | 28 |
| 24467 | TCATCTTCTTGTGGAGCT | coding | 1595-1612 | 101 | — | 29 |
| 24468 | CCATCTGCACGGCCATTG | coding | 1637-1654 | 72 | 28 | 30 |
| 24469 | GTCCAAACATACTTAACG | coding | 1705-1722 | 68 | 32 | 31 |
| 24470 | TATCTGCATCAATTTGTC | coding | 1735-1752 | 83 | 17 | 32 |
| 24471 | ACCGAAAAGCACCAACTG | coding | 1774-1791 | 80 | 20 | 33 |
| 24472 | CTTGTCCTTAGCAAGACA | coding | 1802-1819 | 65 | 35 | 34 |
| 24473 | TCAGGGTGGCTTAAAGAA | coding | 1841-1858 | 53 | 47 | 35 |
| 24474 | ATCCATTTTCAACACAGT | coding | 1882-1899 | 71 | 29 | 36 |
| 24475 | GCCCTTATATGAGAAACA | coding | 1929-1946 | 48 | 52 | 37 |
| 24476 | CAATTTGAAAGAAGTCCT | stop | 3527-3544 | 99 | 01 | 38 |

TABLE 1-continued

Inhibition of human integrin α4 protein
levels by antisense oligonucleotides

| ISIS # | Sequence | Target region | Target site | % Control | % Inhib | SEQ ID NO |
|---|---|---|---|---|---|---|
| 24477 | TCCATCTCTCAATTTGA | 3'-UTR | 3537-3554 | 43 | 57 | 39 |
| 24478 | GGCGGGCTGTTTTCATT | 3'-UTR | 3549-3566 | 115 | — | 40 |

All oligonucleotides have phosphorothioate (P = S or PS) backbones and 2'-methoxyethoxy (2'MOE) "wings" flanking a 2'deoxy gap. 2'MOE nucleotides are shown in bold. All cytosines are 5-methyl cytosines (5meC). Target site refers to nucleotide numbers on the target (Genbank accession No. L12002; SEQ ID NO: 1).

TABLE 2

Dose response effect of antisense oligonucleotides on integrin α4 protein expression

| ISIS # | DOSE (nM) | SEQ ID NO: | % CONTROL 48 hr | % INHIB 48 hr | % CONTROL 72 hr | % INHIB 72 HR |
|---|---|---|---|---|---|---|
| 24451 | 50 | 13 | 63 | 37 | ND | ND |
|  | 100 |  | 44 | 56 | ND | ND |
|  | 200 |  | 34 | 66 | ND | ND |
|  | 400 |  | 44 | 56 | ND | ND |
| 24453 | 50 | 15 | 79 | 21 | 78 | 22 |
|  | 100 |  | 95 | 05 | 93 | 07 |
|  | 200 |  | 38 | 62 | 64 | 36 |
|  | 400 |  | 41 | 59 | 58 | 42 |
|  | 50 | 35 | 77 | 23 | 85 | 35 |
|  | 100 |  | 49 | 51 | 77 | 23 |
|  | 200 |  | 39 | 61 | 61 | 39 |
|  | 400 |  | 42 | 58 | 56 | 44 |
| 24475 | 50 | 37 | 60 | 40 | 69 | 31 |
|  | 100 |  | 31 | 69 | 44 | 56 |
|  | 200 |  | 30 | 70 | ND | ND |
|  | 400 |  | 39 | 61 | 52 | 48 |
| 24477 | 50 | 39 | 56 | 44 | 72 | 28 |
|  | 100 |  | 47 | 53 | 67 | 33 |
|  | 200 |  | 34 | 66 | 44 | 56 |
|  | 400 |  | 35 | 65 | 53 | 47 |

Example 10
Dose Response Curves for Effect of Antisense Oligonucleotides on Integrin α4 Protein Expression An additional series of oligonucleotides were tested for effects on integrin α4 protein expression and compared to active compounds from the previous screens. These oligonucleotides are targeted to an integrin α4 promotor sequence (Rosen et al., Proc. Natl. Acad. Sci. 1991, 88, 4094–4098; GenBank Accession No. M62841, provided herein as SEQ ID NO: 41). These oligonucleotides are shown in Table 3 and their effects on integrin α4 protein expression is shown in Table 4. Where backbones are mixed, linkages are shown as "s" for phosphorothioate (P=S or PS) and "o" for phosphodiester (P=O or PO). Where target region is indicated as 'M62841,' oligonucleotides are targeted to the promotor region whose sequence is described in GenBank Accession No. M62841. Remaining oligonucleotides are targeted to the sequence described in Genbank Accession No. L12002 and their target sites on the L12002 sequence are indicated.

A mouse sequence (SEQ ID NO:47) is included for comparison. It is targeted to the same mRNA region as the human sequence 27104 (coding region just downstream from the AUG codon) and contains 3 mismatches with the human mRNA target.

TABLE 3

Additional oligonucleotides targeted to human integrin α4

| ISIS # | Sequence | Chemistry | Target region | Target site | SEQ ID NO |
|---|---|---|---|---|---|
| 24475 | GCCCTTATATGAGAAACA | PS; 2' MOE/deoxy; All 2' MOE C's are 5 meC | coding | 1929-1946 | 37 |
| 24739 | TTTAGTGACAAAGACGTTAT | PS; deoxy |  | M62841 | 0409-0428 | 42 |

TABLE 3-continued

Additional oligonucleotides targeted to human integrin α4

| ISIS # | Sequence | Chemistry | Target region | Target site | SEQ ID NO |
|---|---|---|---|---|---|
| 24740 | GAAGGCCCCTGGGGAACATT | PS; deoxy | M62841 | 0428-0447 | 43 |
| 24741 | AGACGTTATGGCTATTCTCT | PS; deoxy | M62841 | 0398-0417 | 44 |
| 24742 | TTTAGTGACAAAGACGTTAT | PS; 2'MOE; all C = 5meC | M62841 | 0409-0428 | 42 |
| 24743 | GAAGGCCCCTGGGGAACATT | PS; 2'MOE; all C = 5meC | M62841 | 0428-0447 | 43 |
| 24744 | AGACGTTATGGCTATTCTCT | PS; 2'MOE; all C = 5 meC | M62841 | 0398-0417 | 44 |
| 26643 | TTGCCCTTATATGAGAAACA | PS; 2' MOE; all C = 5 meC | coding | 1929-1948 | 45 |
| 27104 | CCCAAGCCATGCGCTCTCGG | PS/2'MOE; all C = 5 meC | human coding | 0421-0440 | 46 |
| 27108 | CoCoCoAsAsGsCsCsAsTsGsCs GoCoToCoToCoGoG | PO/PS; 2' MOE/deoxy; All C = 5meC | human coding | 0421-0440 | 46 |
| 17044 mouse | CCGCAGCCATGCGCTCTTGG | PS; 2' MOE/deoxy; All 2' MOE C's are 5 meC | mouse coding | | 47 |
| 27109 mouse | CoCoGoCsAsGsCsCsAsTsGsCs GoCoToCoToTOGoG | PO/PS; 2' MOE/deoxy; All C = 5meC | mouse coding | | 47 |

TABLE 4

Dose response curves for effect of antisense oligonucleotides on human integrin α4 protein expression

| ISIS # | Oligo. Conc (nM) | % Control | % Inhib. | SEQ ID NO. |
|---|---|---|---|---|
| 24475 | 10 | 97 | 03 | 37 |
| | 30 | 73 | 27 | |
| | 100 | 84 | 16 | |
| | 300 | 55 | 45 | |
| 24739 | 10 | 69 | 31 | 42 |
| | 30 | 67 | 33 | |
| | 100 | 121 | — | |
| | 300 | 107 | — | |
| 24740 | 10 | 122 | — | 43 |
| | 30 | 119 | — | |
| | 100 | 106 | — | |
| | 300 | 88 | 12 | |
| 24741 | 10 | 109 | — | 44 |
| | 30 | 113 | — | |
| | 100 | 125 | — | |
| | 300 | 127 | — | |
| 24742 | 10 | 112 | — | 42 |
| | 30 | 107 | — | |
| | 100 | 123 | — | |
| | 300 | 128 | — | |
| 24743 | 10 | 96 | 04 | 43 |
| | 30 | 121 | — | |
| | 100 | 117 | — | |
| | 300 | 105 | — | |
| 24744 | 10 | 121 | — | 44 |
| | 30 | 110 | — | |
| | 100 | 118 | — | |
| | 300 | 118 | — | |
| 26643 | 10 | 90 | 10 | 45 |
| | 30 | 95 | 05 | |
| | 100 | 93 | 07 | |
| | 300 | 66 | 34 | |
| 27104 | 10 | 69 | 31 | 46 |
| | 30 | 64 | 36 | |
| | 100 | 49 | 51 | |
| | 300 | 39 | 61 | |
| 17044 mouse | 10 | 86 | 14 | 47 |
| | 30 | 73 | 27 | |
| | 100 | 60 | 40 | |
| | 300 | 58 | 42 | |
| 27108 | 10 | 69 | 31 | 46 |
| | 30 | 95 | 05 | |
| | 100 | 64 | 36 | |
| | 300 | 49 | 51 | |
| 27109 | 10 | 109 | — | 47 |
| | 30 | 114 | — | |
| | 100 | 77 | 23 | |
| | 300 | 55 | 45 | |

In this assay, oligonucleotides 24475, 27104 and 27108 rated 40% inhibition or greater and are preferred. The nucleotide sequence (SEQ ID NO: 47) targeted to mouse in α4, which has only three mismatches with the human target, also showed >40% inhibition at the highest dose.

Example 11

Screening of Additional Oligonucleotide Screening for Inhibition of Integrin α4 Protein Levels New oligonucleotides 26640, 26641, 26642 and 26644 were synthesized and compared against previously tested oligonucleotides. Oligonucleotides are shown in Table 5 and their effect on integrin α4 protein levels is shown in Table 6. Target sites refer to nucleotide numbers on the target sequence (GenBank Accession No. L12002) to which the oligonucleotides hybridize.

TABLE 5

Additional oligonucleotides targeted to human integrin α4

| ISIS # | Sequence | Chemistry | Target region | Target site | SEQ ID NO. |
|---|---|---|---|---|---|
| 26640 | CCACTGATTGTCTCTCTCTT | PS; 2'MOE/deoxy; All C = 5meC | coding | 0789-0806 | 13 |
| 26641 | GAGCTTATTTTCATTCTTTA | PS; 2'MOE/deoxy; All C = 5meC | coding | 0889-0906 | 15 |
| 26642 | TCAGGGTGGCTTAAAGAAGC | PS; 2'MOE/deoxy; All C = 5meC | coding | 1841-1858 | 35 |
| 26644 | TTTCCATTCTCTCAATTTGA | Ps; 2'MOE/deoxy; All C = 5meC | 3'-UTR | 3537-3554 | 37 |

TABLE 6

Dose response curves for effect of antisense oligonucleotides on human integrin α4 protein expression

| ISIS # | Oligo. Conc (nM) | % Control | % Inhib. | SEQ ID NO. |
|---|---|---|---|---|
| 27104 | 10 | 84 | 16 | 46 |
|  | 30 | 82 | 18 |  |
|  | 100 | 59 | 41 |  |
|  | 300 | 37 | 63 |  |
| 17044 | 10 | 97 | 03 | 47 |
|  | 30 | 84 | 16 |  |
|  | 100 | 68 | 32 |  |
|  | 300 | 39 | 61 |  |
| 24451 | 10 | 96 | 04 | 13 |
|  | 30 | 77 | 23 |  |
|  | 100 | 66 | 34 |  |
|  | 300 | 35 | 65 |  |
| 26640 | 10 | 91 | 09 | 13 |
|  | 30 | 83 | 17 |  |
|  | 100 | 62 | 38 |  |
|  | 300 | 35 | 65 |  |
| 24453 | 10 | 88 | 12 | 15 |
|  | 30 | 90 | 10 |  |
|  | 100 | 80 | 20 |  |
|  | 300 | 43 | 57 |  |
| 26641 | 10 | 88 | 12 | 15 |
|  | 30 | 85 | 15 |  |
|  | 100 | 67 | 33 |  |
|  | 300 | 31 | 69 |  |
| 24473 | 10 | 103 | — | 35 |
|  | 30 | 92 | 08 |  |
|  | 100 | 81 | 19 |  |
|  | 300 | 47 | 53 |  |
| 26642 | 10 | 84 | 16 | 35 |
|  | 30 | 77 | 23 |  |
|  | 100 | 56 | 44 |  |
|  | 300 | 23 | 77 |  |
| 24477 | 10 | 83 | 17 | 39 |
|  | 30 | 80 | 20 |  |
|  | 100 | 63 | 37 |  |
|  | 300 | 33 | 67 |  |
| 26644 | 10 | 99 | 01 | 39 |
|  | 30 | 94 | 06 |  |
|  | 100 | 78 | 22 |  |
|  | 300 | 48 | 52 |  |

In this assay, oligonucleotides 27104, 24451, 26640, 24453, 26642, 24477 and 26644 demonstrated 40% inhibition or greater and are preferred. The oligonucleotide sequence (SEQ ID NO: 47) targeted to mouse integrin α4, which has only three mismatches with the human gene target, also showed >40% inhibition at the highest dose.

Example 12

Antisense Inhibition of Murine Integrin α4 mRNA Expression in Mouse P388D (IL-1) Cells Because many conditions which are believed to be ameliorable by antisense oligonucleotides targeted to integrin α4 are not amenable to study in humans, a series of oligonucleotides was designed to target the murine integrin α4 using the published sequence of De Miersman et al., *DNA* 13:743–754; GenBank Accession No:L20788, provided herein as SEQ ID NO: 48). These oligonucleotides are shown in Table 7. Nucleotide bases shown in bold are 2'-methoxyethoxy (2'MOE); remaining positions are 2' deoxy. Target site refers to the first nucleotide position on the target (GenBank Accession No. L20788) to which the oligonucleotide binds.

Oligonucleotides were initially screened in murine P388D (IL-1) macrophage cells (American Type Culture Collection, Manassas Va.) for 4 hours at an oligonucleotide concentration of 100 nM in 3 ug/ml lipofectin. Cells were harvested and RNA was purified by cellular lysis using Catrimox-14 solution (Iowa Biotechnology Corp, Oakdale, Iowa Dahle, C. E. and Macfarlane, D. E., *BioTechniques* 1993, 15, 1–4. RNA was electrophoresed on a 1% agarose/ 1.1% formaldehyde gel with 18 ug RNA loaded in each lane. The integrin α4 probe was a PCR-labeled 1025-base integrin α4 fragment (positions 3681–4706) made by RT-PCR according to the method of Bednarczuk et al. (*Biotechniques* 1991 10,478). Results of the screen are shown in Table 8.

TABLE 7

Antisense oligonucleotides targeted to murine integrin α4

| ISIS # | Sequence | Chemistry | Target region | Target site | SEQ ID NO |
|---|---|---|---|---|---|
| 15600 | CACGCCCCGTTTCTGTGGCC | PS; 2'-MOE, All C = 5meC | 5' cap | 0952-0971 | 49 |
| 15601 | CACGCCCCGTTTCTGTGGCC | PO; 2'-MOE, All C = 5meC | 5' cap | 0952-0971 | 49 |
| 15602 | CACGCCCCGTTTCTGTGGCC | PS; DNA | 5' cap | 0952-0971 | 49 |
| 15603 | GGATGCTTCAGGCTCTGGCC | PS; DNA | 5' UTR | 0972-0991 | 50 |
| 15604 | GGAGCGATCGTAGTGGCCAG | PS; DNA | 5' UTR | 0992-1011 | 51 |
| 15605 | CCGGTGCTGGCAGGCGACAG | PS; DNA | 5' UTR | 1061-1080 | 52 |
| 15606 | GATGAAGTGCAGCAGCGTGT | PS; DNA | 5' UTR | 1081-1100 | 53 |
| 15607 | GGCCACTGACCAGAGTTGCA | PS; DNA | 5' UTR | 1141-1160 | 54 |
| 15608 | CCGCAGCCATGCGCTCTTGG | PS; DNA | AUG | 1183-1202 | 47 |
| 15609 | CACCTCGCTTCCGCAGCCAT | PS; DNA | AUG | 1193-1212 | 55 |

TABLE 8

Antisense inhibition of murine integrin α4 mRNA expression

| ISIS No. | % Control | % Inhib | Seq ID NO: |
|---|---|---|---|
| 15600 | 93 | 07 | 49 |
| 15601 | 60 | 40 | 49 |
| 15602 | 48 | 52 | 49 |
| 15603 | 38 | 62 | 50 |
| 15604 | 134 | — | 51 |
| 15605 | 84 | 16 | 52 |
| 15606 | 72 | 28 | 53 |
| 15607 | 26 | 74 | 54 |
| 15608 | 16 | 84 | 47 |
| 15609 | 07 | 93 | 55 |

As shown in Table 8, ISIS 15607, targeted to the 5'UTR, and ISIS 15608 and 15609, both targeted to the translation initiation codon, were most active in this assay. Dose response curves for ISIS 15607, 15608 and 15609 are shown in Table 9. Results are averages of duplicate samples.

TABLE 9

Antisense inhibition of murine integrin α4 mRNA expression-dose responses

| ISIS No. | Oligo. Conc (nM) | % control | % inhib. | SEQ ID NO: |
|---|---|---|---|---|
| 15607 | 12.5 | 78 | 22 | 54 |
|  | 25 | 67 | 33 |  |
|  | 50 | 50 | 50 |  |
|  | 100 | 55 | 45 |  |
| 15608 | 12.5 | 59 | 41 | 47 |
|  | 25 | 29 | 71 |  |
|  | 50 | 23 | 77 |  |
|  | 100 | 39 | 61 |  |
| 15609 | 12.5 | 54 | 46 | 55 |
|  | 25 | 24 | 76 |  |
|  | 50 | 28 | 72 |  |
|  | 100 | 57 | 43 |  |

Example 13

Antisense Inhibition of Murine Integrin α4 Protein Expression

Murine IC-21 macrophage cells (American Type Culture Collection, Manassas, Va.) were used for further study. Additional oligonucleotides were designed to target murine integrin α4. These are shown in Table 10; all 2' MOE nucleotides are shown in bold and remaining positions are 2' deoxy. All 2'-MOE cytosines in these compounds are 5' methylcytosines. IC-21 cells were seeded at $5 \times 10^4$ cells/well in 24 well plates two days before assay. Cells were treated with 3 ug/ml LIPOFECTIN for 4 hours with 25 nM oligonucleotide. Wells were triplicates. Cells were harvested with 2 mM EDTA after 20 hours and analyzed by flow cytometry as described in Example 8, using CD49d-phycoerythrin (CD49d-PE) antibody conjugate (clone R1-2) and Rat IgG2B-PE as control. Results are shown in Table 11.

TABLE 10

Antisense oligonucleotides targeted to murine integrin α4

| ISIS # | Sequence | Chemistry | Target region | Target site | SEQ ID NO: |
|---|---|---|---|---|---|
| 15607 | GGCCACTGACCAGAGTTGCA | PS; 2' deoxy | 5' UTR | 1141-1160 | 54 |
| 16477 | CGGACCAGTACCAGGGTTAC | PS; 2' deoxy | scrambled | | 56 |
| 16428 | GGCCACTGACCAGAGTTGCA | PS; 2' MOE/deoxy | 5' UTR | 1141-1160 | 54 |
| 16429 | GGCCACTGACCAGAGTTGCA | PS; 2' MOE/deoxy | 5' UTR | 1141-1160 | 54 |
| 16430 | GGCCACTGACCAGAGTTGCA | PS; 2' MOE/deoxy | 5'UTR | 1141-1160 | 54 |
| 15608 | CCGCAGCCATGCGCTCTTGG | PS; DNA | AUG | 1183-1202 | 47 |
| 16478 | GCCGACACCCGTTCGTTCGG | PS; DNA | scrambled | | 57 |
| 16431 | CCGCAGCCATGCGCTCTTGG | PS; 2' MOE/deoxy | AUG | 1183-1202 | 47 |
| 16432 | CCGCAGCCATGCGCTCTTGG | PS; 2' MOE/deoxy | AUG | 1183-1202 | 47 |
| 16433 | CCGCAGCCATGCGCTCTTGG | PS; 2' MOE/deoxy | AUG | 1183-1202 | 47 |
| 15609 | CACCTCGCTTCCGCAGCCAT | PS; DNA | AUG | 1193-1212 | 55 |
| 16479 | ACCTCCTCGCTCACGCGCTA | PS; DNA | Scrambled | | 58 |
| 16434 | CACCTCGCTTCCGCAGCCAT | PS; 2' MOE/deoxy | AUG | 1183-1202 | 47 |
| 16435 | CACCTCGCTTCCGCAGCCAT | PS; 2' MOE/deoxy | AUG | 1183-1202 | 47 |
| 16436 | CACCTCGCTTCCGCAGCCAT | PS; 2' MOE/deoxy | AUG | 1183-1202 | 47 |
| 16437 | CGCTTCCGCAGCCATGCGCT | PS; 2' MOE/deoxy | AUG | 1188-1207 | 59 |

All 2'MOE cytosines in Table 10 are 5-methylcytosines.

TABLE 11

Inhibition of integrin α4 protein expression by antisense oligonucleotides

| ISIS No. | % Control | % Inhib | Seq ID NO: |
|---|---|---|---|
| 15607 | 82 | 18 | 54 |
| 16477 | 96 | 04 | 56 |
| 16428 | 67 | 33 | 54 |
| 16429 | 60 | 40 | 54 |
| 16430 | 50 | 50 | 54 |
| 15608 | 63 | 37 | 47 |
| 16478 | 92 | 08 | 57 |
| 16431 | 35 | 65 | 47 |
| 16432 | 53 | 47 | 47 |
| 16433 | 23 | 77 | 47 |
| 15609 | 57 | 43 | 55 |
| 16479 | 96 | 04 | 58 |
| 16434 | 33 | 67 | 47 |
| 16435 | 30 | 70 | 47 |
| 16436 | 47 | 53 | 47 |
| 16437 | 36 | 64 | 59 |

ISIS 16430, 16431, 16433, 16434, 16434, 16435, 16436 and 16437 gave better than 50% inhibition in this assay and are preferred.

Dose responses for effect of ISIS 16431 and 16433 on integrin α4 protein levels are shown in Table 12. Cells (triplicates) were seeded at 2.5×10⁴ cells/well in 24-well plates the day before treatment. Oligonucleotide concentrations were 0.2, 1, 5, 25 and 50 nM in 3 ug/ml LIPOFECTIN. Cells were harvested with 2 mM EDTA for 4 minutes, then 1 ml of 2% BSA, 0.2% azide was added per contents of each well. Protein levels were analyzed by flow cytometry as described in Example 8, using CD49d-PE antibody conjugate at 2 ug/ml, and rat IgG2B at 2 ug/ml as control. ISIS 16431 and 16433 were found to have IC50s of approximately 1 nM for integrin α4 protein inhibition.

TABLE 12

Dose response effect of 16431, 16433 on integrin α4 protein levels

| ISIS No. | Dose (nM) | % of control | % inhib. | SEQ ID NO: |
|---|---|---|---|---|
| 16431 | 0.2 | 82 | 18 | 47 |
| | 1 | 57 | 43 | |
| | 5 | 34 | 66 | |
| | 25 | 32 | 68 | |
| | 50 | 30 | 70 | |
| 16433 | 0.2 | 85 | 15 | 47 |
| | 1 | 62 | 38 | |
| | 5 | 37 | 63 | |
| | 25 | 20 | 80 | |
| | 50 | 30 | 70 | |
| 16478 | 5 | 95 | 05 | 57 |
| | 25 | 87 | 13 | |
| | 50 | 84 | 16 | |

Another dose-response experiment on ISIS 16433 was done with scramble control included. IC-21 cells were treated with 0.3, 1, 3, 10 and 30 nM oligonucleotide with 3 ug/ml LIFOFECTIN for 4 hours. Cells were incubated for 24 hours, harvested with trypsin, stained with 2 ug/ml CD49d-PE and rat IgG2Bas in previous examples. The results are shown in Table 13. ISIS 16433 at 30 nM was found to inhibit protein levels to below basal levels.

TABLE 13

Dose response effect of 16431, 16433 on integrin α4 protein levels

| ISIS No. | Oligo. Conc. (nM) | % of control | % inhib. | SEQ ID NO: |
|---|---|---|---|---|
| 16433 | 0.3 | 89 | 11 | 47 |
|  | 1 | 68 | 32 |  |
|  | 3 | 25 | 75 |  |
|  | 10 | 03 | 97 |  |
|  | 30 | −14 | (100) |  |
| 16478 | 0.3 | 137 | — | 57 |
|  | 1 | 131 | — |  |
|  | 3 | 127 | — |  |
|  | 10 | 130 | — |  |
|  | 30 | 108 | — |  |

Another dose response experiment was done to determine the IC50 of ISIS 16433 for inhibition of integrin α4 RNA. IC-21 cells were treated in duplicate with ISIS 16433 at 6.25, 12.5, 25 or 50 nM with 3 ug/ml LIPOFECTIN.

RNA was purified with Qiagen Qiashredder/RNEASY™ Kit according to manufacturer's directions. Probes were random primed using a Prime-a-Gene Kit (Promega, Madison, Wis.). The results are shown in Table 14. ISIS 16433 was shown to have an IC50 of approximately 10 nM for integrin α4 RNA reduction.

TABLE 14-continued

Dose response effect of ISIS 16433 on integrin α4 RNA levels

| ISIS No. | Oligo dose (nM) | Percent of control | Percent inhib. | SEQ ID NO: |
|---|---|---|---|---|
| 16478 | 6.25 | 75 | 25 | 57 |
|  | 12.5 | 60 | 40 |  |
|  | 25 | 24 | 76 |  |
|  | 50 | 26 | 74 |  |

Example 14

Additional Antisense Oligonucleotides Targeted to Murine Integrin α4-optimization Additional oligonucleotides were synthesized with the ISIS 16433 sequence (SEQ ID NO: 47, targeted to the translation initiation codon) in order to optimize the backbone chemistry and 2' methoxyethoxy gap placement. These compounds were tested for ability to inhibit integrin α4 protein expression. Compounds and results are shown in Tables 15 and 16. ISIS 17044 was found to reduce integrin α4 expression to below starting levels and was chosen for further study in animal models of disease.

TABLE 15

Optimization of oligonucleotides having SEQ ID NO: 47

| ISIS No. | Sequence | Chemistry |
|---|---|---|
| 17044 | CCGCAGCCATGCGCTCTTGG | All PS; 2' MOE/deoxy; All 2' MOE C's are 5 meC |
| 17045 | CCGCAGCCATGCGCTCTTGG | All PS; 2' MOE/deoxy; All 2' MOE C's are 5 meC |
| 17046 | CCGCAGCCATGCGCTCTTGG | All PS; 2' MOE/deoxy; All 2' MOE C's are 5 meC |
| 17047 | CCGCAGCCATGCGCTCTTGG | All PS; 2' MOE/deoxy; All 2' MOE C's are 5 meC |
| 17160 | COCsGsCsAsGsCsCsAsTsGsCsGoCoToCoToToGoG | PO/PS; All 2'MOE; 5meC at positions 1, 2, 14, 16 |
| 16433 | CCGCAGCCATGCGCTCTTGG | All PS; 2' MOE/deoxy; All 2' MOE C's are 5 meC |
| 17048 | GCCGACACCCGTTCGTTCGG (scrambled control; SEQ ID NO: 57) | All PS; 2' MOE/deoxy; All 2' MOE C's are 5 meC |

Internucleoside backbone linkages are uniform P = S except for ISIS 17160. "o" indicates a phosphodiester (P = O) linkage and "s" indicates a phosphorothioate (P = S) linkage.

TABLE 14

Dose response effect of ISIS 16433 on integrin α4 RNA levels

| ISIS No. | Oligo dose (nM) | Percent of control | Percent inhib. | SEQ ID NO: |
|---|---|---|---|---|
| 16433 | 6.25 | 59 | 41 | 47 |
|  | 12.5 | 46 | 44 |  |
|  | 25 | 28 | 72 |  |
|  | 50 | 43 | 57 |  |

TABLE 16

Dose response for optimization of oligonucleotides with SEQ ID NO: 47

| ISIS No. | Oligo. Conc (nM) | % Control | % Inhib. | SEQ ID NO: |
|---|---|---|---|---|
| 17044 | 0.3 | 100 | 0 | 47 |
|  | 1 | 81 | 19 |  |
|  | 3 | 32 | 68 |  |
|  | 10 | −9 | >100 |  |

TABLE 16-continued

Dose response for optimization of oligonucleotides with SEQ ID NO: 47

| ISIS No. | Oligo. Conc (nM) | % Control | % Inhib. | SEQ ID NO: |
|---|---|---|---|---|
| 17045 | 0.3 | 109 | — | 47 |
|  | 1 | 65 | 35 |  |
|  | 3 | 34 | 66 |  |
|  | 10 | 12 | 88 |  |
| 17046 | 0.3 | 161 | — | 47 |
|  | 1 | 123 | — |  |
|  | 3 | 125 | — |  |
|  | 10 | 75 | 25 |  |
| 17047 | 0.3 | 132 | — | 47 |
|  | 1 | 107 | — |  |
|  | 3 | 77 | 23 |  |
|  | 10 | 36 | 67 |  |
| 17160 | 0.3 | 165 | — | 47 |
|  | 1 | 140 | — |  |
|  | 3 | 144 | — |  |
|  | 10 | 160 | — |  |
| 16433 | 0.3 | 146 | — | 47 |
|  | 1 | 94 | 06 |  |
|  | 3 | 64 | 36 |  |
|  | 10 | 02 | 98 |  |
| 17048 (control) | 0.3 | 159 | — | 57 |
|  | 1 | 159 | — |  |
|  | 3 | 150 | — |  |
|  | 10 | 119 | — |  |

Example 15
Mouse Experimental Autoimmune Encephalomyelitis (EAE) Model for Multiple Sclerosis Experimental autoimmune encephalomyelitis (EAE) is an inflammatory, demyelinating central nervous system disease frequently used as an animal model for multiple sclerosis. It is inducible in genetically susceptible animals by immunization with whole spinal cord homogenate or protein components of the myelin sheath such as myelin basic protein (MBP) or proteolipid protein (PLP), or by transfer of MBP- or PLP- specific T cells. Myers et al., *J. Immunol.* 1993, 151, 2252–2260.

CSJLF-1 mice (Jackson Laboratory, Bar Harbor, Me.) were immunized with the p13 peptide (HSLGKWLGHPDKF-amide, synthesized by Research Genetics, Huntsville, Ala., SEQ ID NO. 60) which corresponds to residues 139–151 of PLP and is encephalitogenic in these mice. Mice were immunized essentially as described in Myers et al., (*J. Neuroimmunology* 1992, 41, 1–8). Briefly, mice were injected in the hind footpads and the base of the tail with 50–100 ug of p13 peptide, emulsified in CFA (Difco, Detroit, Mich.) fortified with 4 mg/ml of heat-killed H37Ra *Mycobacterium tuberculosis* bacteria (Difco). At the time of footpad injections and again 2 days later, mice were also injected intravenously with 500 ng of pertussis toxin (Sigma, St. Louis, Mo.).

Mice were treated with the antisense oligonucleotide ISIS 17044 at various doses, beginning one day before p13 immunization except where indicated otherwise. Oligonucleotide was formulated in 0.9% saline and was administered daily by subcutaneous injection, with dosing continuing until more than 50% of the p13-immunized but saline-treated control group began showing symptoms of disease. Dosing was then terminated and mice were observed for effects of treatment on the course of disease. Disease severity was scored on a scale of 0 to 5 with 0=no symptoms, 1=flaccid tail, 2=hind limb weakness, 3=hind limb paralysis, 4=hind and front limb paralysis and 5=moribund or dead. Time until disease onset was also measured and compared to p13-immunized control mice that received saline instead of oligonucleotide.

Example 16
EAE Experiment 1

Mice were treated with ISIS 17044 as described in Example 15, at daily doses ranging from 1 mg/kg to 20 mg/kg, injected subcutaneously (SC). Mean peak disease severity and average number of days to disease onset were measured and these are shown in Table 17.

TABLE 17

EAE Experiment 1- effects of ISIS 17044 on EAE

| Group | Disease Incidence | Peak Severity | Days to Onset |
|---|---|---|---|
| Saline | 6/7 | 1.57 | 14.5 |
| 17044 20 mg/kg | 5/7 | 1.43 | 15 |
| 17044 10 mg/kg | 4/7 | 2.0 | 12.75 |
| 17044 5 mg/kg | 6/7 | 1.86 | 17 |
| 17044 1 mg/kg | 4/7 | 0.29 | 17.25 |

As shown, 17044 reduced disease severity or delayed disease onset.

Example 17
EAE Experiment 2

Mice were treated with ISIS 17044 as described in Example 15, at daily doses ranging from 0.3 mg/kg to 3 mg/kg, injected subcutaneously, and 1 mg/kg injected intravenously for comparison. Mean peak disease severity and average number of days to disease onset were measured and these are shown in Table 18.

TABLE 18

EAE Experiment 2- effects of ISIS 17044 on EAE

| Group | Disease Incidence | Peak Severity | Days to Onset |
|---|---|---|---|
| Saline | 7/7 | 2/43 | 13.7 |
| 17044 3 mg/kg SC | 7/7 | 2.29 | 16.4 |
| 17044 1 mg/kg SC | 4/7 | 1.0 | 18.25 |
| 17044 0.3 mg/kg SC | 7/7 | 2.14 | 16.57 |
| 17044 1 mg/kg IV | 5/7 | 1.42 | 17.2 |

As shown, 17044 reduced disease severity and delayed disease onset at all concentrations.

Example 18
EAE Experiment 3

Mice were treated with ISIS 17044 as described in Example 15, at daily doses ranging from 0.5 mg/kg to 2.0 mg/kg, injected subcutaneously (SC). A thrice-weekly dosing regimen was also tested, and a scrambled control (ISIS 17614, GCCGACACCCGTTCGTTCGG, 2' MOE /deoxy; P=S; SEQ ID NO: 57) was also tested. Disease severity and time until disease onset were measured and these are shown in Table 19.

TABLE 19

EAE Experiment 3- effects of ISIS 17044 on EAE

| Group | Disease Incidence | Peak Severity | Days to Onset |
|---|---|---|---|
| Saline | 7/7 | 2.29 | 15.14 |
| 17044 2 mg/kg | 2/6 | 0.83 | 20 |
| 17044 1.5 mg/kg | 4/7 | 1.5 | 17.5 |
| 17044 1.0 mg/kg | 4/5 | 1.5 | 19.25 |
| 17044 0.5 mg/kg | 5/6 | 1.5 | 21.4 |
| 17044 1 mg/kg 3× weekly | 6/7 | 1.0 | 20.3 |
| 17614 1 mg/kg | 7/7 | 2.14 | 16.86 |

As shown, 17044 reduced disease severity or delayed disease onset.

Example 19
EAE Experiment 4-Prophylactic vs. Therapeutic Dosing

Mice were treated with ISIS 17044 as described in Example 15, at daily doses of 0.01 /kg to 2.0 mg/kg, injected subcutaneously (SC). The scrambled control oligonucleotide, ISIS 17614, was also tested at 2 mg/kg. A 1 mg/kg daily dose, given therapeutically was also tested. In this regimen, oligonucleotide treatment began on day 18, after animals had begun showing symptoms of paralysis, and continued until day 31. Disease severity and time until disease onset were measured and these are shown in Table 20.

TABLE 20

EAE Experiment 4- effects of ISIS 17044 on EAE-Therapeutic (T) vs. Prophylactic (P) Regimen

| Group | Disease Incidence | Peak Severity | Days to Onset |
|---|---|---|---|
| Saline | 6/7 | 3.29 | 16 |
| 17044 2.0 mg/kg SC (P) | 7/7 | 2.29 | 16.71 |
| 17044 1.0 mg/kg SC (P) | 5/5 | 2.2 | 15 |
| 17044 0.1 mg/kg SC (P) | 7/7 | 1.57 | 16.29 |
| 17044 0.01 mg/kg (P) | 6/7 | 1.86 | 13.83 |
| 17044 1 mg/kg (T) | 6/6 | 1.83 | 13.3 |
| 17614 2 mg/kg SC (control) | 7/7 | 1.86 | 14.14 |

As shown, 17044 reduced disease severity when given therapeutically (time to disease onset is not expected to be increased because dosing begins after onset of disease).

Example 20
EAE Experiment 5-Prophylactic vs. Therapeutic Dosing

Mice were treated with ISIS 17044 as described in Example 15, at daily doses of 0.01 /kg to 2.0 mg/kg, injected subcutaneously (SC). The scrambled control oligonucleotide, ISIS 17614, was also tested at 2 mg/kg. A 1 mg/kg daily dose, given therapeutically was also tested. In this regimen, oligonucleotide treatment began on day 11, after animals had begun showing symptoms of paralysis, and continued until day 27. Disease severity and time until disease onset were measured and these are shown in Table 21.

TABLE 21

EAE Experiment 5- effects of ISIS 17044 on EAE-Therapeutic (T) vs. Prophylactic (P) Regimen

| Group | Disease Incidence | Peak Severity | Days to Onset |
|---|---|---|---|
| Saline | 6/7 | 1.86 | 10.83 |
| 17044 2.0 mg/kg SC (P) | 7/7 | 1.86 | 12 |
| 17044 1.0 mg/kg SC (P) | 6/7 | 1.86 | 11.33 |
| 17044 0.1 mg/kg SC (P) | 6/7 | 1.14 | 12.67 |
| 17044 0.01 mg/kg (P) | 7/7 | 1.57 | 11.57 |
| 17044 1 mg/kg (T) | 7/7 | 1.42 | 12.71 |
| 17614 2 mg/kg SC (control) | 6/7 | 1.71 | 9 |

As shown, 17044 reduced disease severity when given therapeutically (time to disease onset is not expected to be increased because dosing begins after onset of disease).

Example 21
Mouse Collagen-Induced Arthritis (CIA) Model for Rheumatoid Arthritis A model for human rheumatoid arthritis has been developed wherein mice are immunized with bovine type II collagen. Anderson et al., *J. Immunol.* 1991 147, 1189–1193, citing Trentham et al., *J. Exp. Med* 1977, 146, 857. Swelling and inflammation of the joints follows in approximately 3 weeks, with joint distortion and ankylosis typical of rheumatoid arthritis. This model has been used to study the effects of the antisense oligonucleotide 17044, targeted to mouse integrin $\alpha 4$, on arthritis in mice.

DBA/1LacJ mice were obtained from Jackson Laboratory, Bar Harbor, Me. Female mice aged 6 to 8 weeks were used and assigned to groups, ten mice per group. On day 0 mice were immunized at the base of the tail with 100 ug of bovine type II collagen which was emulsified in Complete Freund's Adjuvant (CFA). On day 7, a second booster dose of collagen was administered by the same route. On day 14 the mice were injected subcutaneously with 100 ug of lipopolysaccharide (LPS). Weights were recorded weekly. Mice were inspected daily for the onset of CIA, which is characterized by erythema and edema. Upon the onset of the disease, paw widths and rear ankle widths of affected and unaffected joints were measured three times a week using a constant tension caliper. In addition, limbs were clinically evaluated and graded 0–4, where 0=normal; 1=one digit swollen; 2=inflammation present in more than one digit; 3=joint distortion with or without inflammation; and 4=ankylosis, detected by joint manipulation. The progression of all measurements was recorded to day 50. At the end of the observation period for each mouse, all paws were removed and examined histologically.

The oligonucleotide, the positive control drug (cyclophosphamide, 5 mg/kg), and the vehicle were administered daily to each mouse intraperitoneally (IP) starting on day −3 and continuing for the duration of the study. Each animal received 10 mg/kg as a bolus daily dose.

Example 22
Effect of Antisense Oligonucleotide Targeted to Integrin $\alpha 4$ on Collagen-Induced Arthritis (CIA)

In a preliminary study, a single 10 mg/kg daily dose of ISPH 17044 was administered from the time of disease induction to the conclusion of the study 50 days later. Arthritis incidence was reduced from 70 to 30% in the ISIS 17044-treated group. A summary of clinical parameters is shown in Table 22.

TABLE 22

Effect of ISIS 17044 on Collagen-Induced Arthritis

| Treatment | Severity | Mean Day of Onset | # Paws/ Mouse | Peak Day of Inflamm. |
|---|---|---|---|---|
| Vehicle | 3.2 ± 1.1 | 19.7 ± 1.1 | 1.2 ± 0.4 | 6.7 ± 2.9 |
| 17044 10 mg/kg | 2.1 ± 1.1 | 20.3 ± 1.9 | 0.7 ± 0.4 | 1.6 ± 0.8 |
| Cyclophosphamide 5 mg/kg | 0 ± 0 | — | 0 ± 0 | — |

Severity = total clinical score/total number of mice in group.
Paws/Mouse = mean number of affected paws at termination/total number of mice in group.

Peak Day of Inflammation=day from onset to time of maximum swelling for each joint measured.

The mice that developed arthritis in the various treatment groups were compared and the results are shown in Table 23.

TABLE 23

Comparison of Mice With Arthritis

| Treatment | Mean # of Paws Involved | Mean Clinical Score |
|---|---|---|
| Vehicle | 1.7 ± 0.4 | 4.6 ± 0.4 |
| 17044 10 mg/kg | 2.3 ± 0.3 | 7.0 ± 1.0 |
| Cyclophosphamide 5 mg/kg | — | — |

Mean # Paws Involved = number paws at termination in the affected mice/number of affected mice in group.
Mean Clinical Score = total clinical score of affected mice/total number of affected mice in group.

Example 23

Reduction of Leukocyte Trafficking into the Central Nervous System of EAE mice by Antisense Oligonucleotide Targeted to Integrin α4

Mice from EAE experiment 3 (Example 18 above) were sacrificed with $CO_2$ and the spinal cord was removed and cut into 0.5 cm pieces through lumbar and low thoracic regions. The pieces were embedded in O.C.T. tissue freezing medium (Ted Pella Inc., Redding, Calif.) on dry ice and methylbutane. Four-micron frozen sections were cut and air dried overnight. The sections were fixed for three minutes in ice-cold acetone and then placed on a Dako Autostainer (Dako Corporation, Carpinteria, Calif.) and treated in the following steps: 5 minutes in 0.03% $H_2O_2$, 5 minutes in 5% donkey serum diluted in PBS, 45 minutes in appropriately diluted primary antibody, 30 minutes in horseradish peroxidase-labeled donkey anti-rat secondary antibody (Jackson Laboratory, Bar Harbor, Me.). Sections were rinsed between treatments with PBS. All the antibodies used were rat anti-mouse from PharMingen (San Diego, Calif.), except BM-8, which was from Bachem Bioscience Inc. (King of Prussia, Pa.). The immunostaining was developed with DAB (Dako Corporation) and counterstained with hematoxylin.

Treatment with 1 mg/kg ISIS 17044 was shown to reduce leukocyte trafficking into the spinal cords and brains of CSJLF1 mice directly immunized to develop EAE. In preliminary experiments, leukocyte trafficking as measured by the expression of VLA-4, of which integrin α4 is one of two subunits, CD4 (a T-cell marker), BM-8 (a macrophage marker) and CD18 (contained in the LFA-1 and MAC-1 adhesion molecules found on leukocytes) was significantly reduced. CD4+T cells were virtually eliminated from the central nervous system of ISIS 17044-treated mice in one experiment. These cells have been shown to be critical for the induction of EAE. In a second experiment (EAE experiment 4, Example 19 above), these results were confirmed, and there appeared to be a dose-dependent effect with 1.0 mg/kg of 17044 causing a greater reduction of leukocyte influx into the central nervous system than did 0.1 mg/kg 17044. Scrambled control oligonucleotide ISIS 17614 was not effective in reducing cellular influx in this experiment.

Example 24

Effect of Antisense Oligonucleotides Targeted to Integrin α4 on Inflammatory Bowel Disease A mouse model for inflammatory bowel disease (IBD) has recently been developed Okayasu et al. (*Gastroenterology* 1990, 98, 694–702). Administration of dextran sulfate to mice induces colitis that mimics human IBD in almost every detail. Dextran sulfate-induced IBD and human IBD have subsequently been closely compared at the histological level and the mouse model has been found to be an extremely reproducible and reliable model. It is used here to test the effect of ISIS 17044 on inflammatory bowel disease.

Female Swiss Webster mice (8 weeks of age) weighing approximately 25 to 30 grams are kept under standard conditions. Mice are allowed to acclimate for at least 5 days before initiation of experimental procedures. Mice are given 5% dextran sulfate sodium in their drinking water (available ad libitum) for 5 days. Concomitantly, ISIS 17044 oligonucleotide in pharmaceutical carrier, carrier alone (negative control) or TGF-β (known to protect against dextran sulfate-mediated colitis in mice) is administered. ISIS 17044 is given as daily subcutaneous injection of 1 mg/kg to 5 mg/kg for 5 days. TGF-β is given as 1 ug/mouse intracolonically.

Mice are sacrificed on day 6 and colons are subjected to histopathologic evaluation. Until sacrifice, disease activity is monitored by observing mice for weight changes and by observing stools for evidence of colitis. Mice are weighed daily. Stools are observed daily for changes in consistency and for presence of occult or gross bleeding. A scoring system is used to develop a disease activity index by which weight loss, stool consistency and presence of bleeding are graded on a scale of 0 to 3 (0 being normal and 3 being most severely affected) and an index is calculated. Drug-induced changes in the disease activity index are analyzed statistically. The disease activity index has been shown to correlate extremely well with IBD in general.

Example 25

Effect of Antisense Oligonucleotide Targeted to Integrin α4 on Survival in Murine Heterotopic Heart Transplant Model To determine the therapeutic effects of integrin α4 antisense oligonucleotide in preventing allograft rejection, the murine integrin α4-specific oligonucleotide ISIS 17044 is tested for activity in a murine vascularized heterotopic heart transplant model. Hearts from Balb/c mice are transplanted into the abdominal cavity of C3H mice as primary vascularized grafts essentially as described by Isobe et al., (*Circulation* 1991, 84, 1246–1255). Oligonucleotide is administered by continuous intravenous administration via a 7-day ALZET pump. The mean survival time for untreated mice is usually approximately 9–10 days. Treatment of the mice for 7 days with 1 mg/kg to 5 mg/kg ISIS 17044 is expected to increase the mean survival time.

Example 26
Effect of Antisense Oligonucleotide Targeted to Integrin α4 on Leukocyte Migration Leukocyte infiltration of tissues and organs is a major aspect of the inflammatory process and contributes to tissue damage resulting from inflammation. The effect of ISIS 17044 on leukocyte migration is examined using a mouse model in which carrageenan-soaked sponges are implanted subcutaneously. Carrageenan stimulates leukocyte migration and edema. Effect of oligonucleotide on leukocyte migration in inflammatory exudates is evaluated by quantitation of leukocytes infiltrating the implanted sponges. Following a four hour fast, 40 mice are assigned randomly to eight groups each containing five mice. Each mouse is anesthetized with METOFANE and a polyester sponge impregnated with 1 ml of a 20 mg/ml solution of carrageenan is implanted subcutaneously. Saline is administered intravenously to Group 1 at 10 ml/kg four hours prior to sponge implantation and this serves as the vehicle control. Indomethacin (positive control) is administered orally at 3 mg/kg at a volume of 20 ml/kg to Group 2 immediately following surgery, again 6–8 hours later and again at 21 hours post-implantation. ISIS 17044 is administered intravenously at a dose of 1 mg/kg to 5 mg/kg to Group 3 four hours prior to sponge implantation. ISIS 17044 is administered intravenously at a dose of 1 mg/kg to 5 mg/kg to Group 4 immediately following sponge implantation. ISIS 17044 is administered intravenously at 1 mg/kg to 5 mg/kg to Groups 5, 6, 7 and 8 at 2, 4, 8 and 18 hours following sponge implantation, respectively. Twenty-four hours after implantation, sponges are removed, immersed in EDTA and saline (5 ml) and squeezed dry. Total numbers of leukocytes in sponge exudate mixtures are determined. The oral administration of indomethacin at 3 mg/kg generally produces a 75–80% reduction in mean leukocyte count when compared to the vehicle control group.

Example 27
Experimental Metastasis Assay

To evaluate the role of integrin α4 in metastasis, experimental metastasis assays are performed by injecting 1 ×10⁵ C8161 cells into the lateral tail vein of athymic nude mice. C8161 is a human melanoma cell line. Treatment of C8161 cells with the cytokine TNF-α and interferon γ has previously been shown to result in an increased number of lung metastases when cells were injected into nude mice (Miller, D. E. and Welch, D. R., *Proc. Am. Assoc. Cancer Res.* 1990, 13, 353). Four-week-old female athymic nude mice (Harlan Sprague Dawley) are used. Animals are maintained under the guidelines of the NIH. Groups of 4–8 mice each are tested in experimental metastasis assays.

Treatment of C8161 cells with antisense oligonucleotide ISIS 27104, complementary to human integrin α4, is performed in the presence of the cationic lipid, LIPOFECTIN (Gibco/BRL, Gaithersburg, Md.). Cells are seeded in 60 mm tissue culture dishes at 10⁶ cells/ml and incubated at 37° C. for 3 days, washed with Opti-MEM (Gibco/BRL) 3 times and 100 μl of Opti-MEM medium is added to each well. 0.5 μM oligonucleotide and 15 μg/ml LIPOFECTIN are mixed at room temperature for 15 minutes. 25 μl of the oligonucleotide-LIPOFECTIN mixture is added to the appropriate dishes and incubated at 37° C. for 4 hours. The oligonucleotide-LIPOFECTIN mixture is removed and replaced with DME-F12 medium containing 10% fetal calf serum. After 4 hours, 500 U/ml TNF-α is added to the appropriate wells and incubated for 18 hours at which time cells are removed from the plates, counted and injected into athymic nude mice. Alternatively, tumor cells (untreated with oligonucleotide) are implanted into athymic nude mice as above and tumor-bearing mice are treated every other day with antisense oligonucleotide at doses of 1 mg/kg to 5 mg/kg.

After 4 weeks, mice are sacrificed, organs are fixed in Bouin's fixative and metastatic lesions on lungs are scored with the aid of a dissecting microscope.

Treatment of C8161 cells with ISIS 27104 decreases the metastatic potential of these cells, and eliminates the enhanced metastatic ability of C8161 which results from TNF-α treatment.

Example 28
Effect of Integrin α4 Antisense Oligonucleotide in a Murine Model for Crohn's Disease SJL/J and IL10−/− mice are used in a TNBS (2,4,5,-trinitrobenzene sulfonic acid) induced colitis model for Crohn's disease (Neurath, M. F., et al., *J. Exp. Med.*, 1995, 182, 1281–1290). Mice between the ages of 6 weeks and 3 months are used to assess the activity of TNF-α antisense oligonucleotides.

C3H/HeJ, SJL/JK and IL10−/− mice are fasted overnight prior to administration of TNBS. A thin, flexible polyethylene tube is slowly inserted into the colon of the mice so that the tip rests approximately 4 cm proximal to the anus. 0.5 mg of the TNBS in 50% ethanol is slowly injected from the catheter fitted onto a 1 ml syringe. Animals are held inverted in a vertical position for approximately 30 seconds. Oligonucleotide ISIS 17044 is administered either at the first sign of symptoms or simultaneously with induction of disease. Animals, in most cases, are dosed every day. Administration is by i.v., i.p., s.q., minipumps or intracolonic injection. Experimental tissues are collected at the end of the treatment regimen for histochemical evaluation.

Example 29
Effect of Antisense Oligonucleotide Targeted to Integrin α4 in a Murine Model for Hepatitis Concanavalin A-induced hepatitis is used as a murine model for hepatitis (Mizuhara, H., et al., *J. Exp. Med.*, 1994, 179, 1529–1537). Female Balb/c and C57BL/6 mice between the ages of 6 weeks and 3 months are used to assess the activity of antisense oligonucleotide ISIS 17044.

Mice are intravenously injected with oligonucleotide. The pretreated mice are then intravenously injected with 0.3 mg concanavalin A (Con A) to induce liver injury. Within 24 hours following Con A injection, the livers are removed from the animals and analyzed for cell death (apoptosis) by in vitro methods. In some experiments, blood is collected from the retro-orbital vein.

Example 30
Effect of Antisense Oligonucleotide Targeted to Integrin α4 in a Murine Model for Asthma Airway inflammation is observed in patients with allergic asthma. A murine model of allergic asthma has been developed, (Hessel et al. *J. Immunol.* 1998, 160, 2998–3005). Sensitization of BALB/c mice with ovalbumin induces a high level of ovalbumin-specific IgE in serum. Inhalation of ovalbumin in sensitized mice causes an immediate bronchoconstrictive response. Repeated inhalation of ovalbumin in sensitized animals induces nonspecific airway hyperresponsiveness in vivo, and infiltration of leukocytes in airway tissue.

Pathogen-free male BALB/c mice (6–8 wk) are obtained from Jackson Laboratories. Active sensitization is performed by seven IP injections of 10 ug of ovalbumin (Sigma Chemical Co, St. Louis, Mo., grade II) in 0.5 ml of pyrogen-free saline on alternate days, one injection per day. This produces high titers of total IgE in mouse serum of which 80% is ovalbumin-specific IgE (Hessel et al., 1998, *J. Immunol.* 160: 2998–3005). Four weeks after the last injection, mice are exposed either to ovalbumin aerosols (2 mg/ml) or saline aerosols, once per day for eight days. The aerosol is generated with a nebulizer such as Medix 8001 (Sussex, UK). Animals were exposed for 5 minutes per aerosol challenge.

Antisense oligonucleotide 17044 is given to the mice during the challenge period. Thirty minutes before the first and fifth inhalation challenge, sensitized mice were injected intravenously with a 1 mg/kg to 5 mg/kg dose of ISIS 17044 in PBS.

Airway responsiveness to methacholine is measured in vivo 24 hours after the last aerosol exposure using the air-overflow pressure method, in which bronchial resistance to inflation is measured. Mice are anesthetized by IP injection of urethan 2 g/kg and placed on a heated blanket. The trachea is cannulated and a small polyethylene catheter is placed in the jugular vein for IV administrations. Spontaneous breathing is suppressed by IV injection of tubocurarine chloride (3.3 mg/kg). When it stopped, the tracheal cannula is attached to a respiration pump. At intervals, increasing doses of methacholine ranging from 40 to 1280 ug/kg were given. The increase in air-overflow pressure (caused by reduction of air flow in to the lungs as a result of increasing airway tone) is measured at its peak and expressed as a percentage increase.

Bronchoalveolar lavage is used to measure the leukocyte infiltration of airway tissue. Three and 24 hours after the last aerosol, mice are anesthetized by IP injection of 0.25 ml of sodium pentobarbitone (60 mg/ml). The abdomen and chest are opened, and the abdominal aorta is excised. Below the larynx, a small incision is made, and a flexible polyethylene cannula is inserted into the trachea and fixed with a ligature. Mice are lavaged five times with 1 ml aliquots of pyrogen-free saline warmed to 37° C. The cells derived from each lavage were pooled, were washed with cold PBS and resuspended in 200 ul of cold PBS. Total numbers of cells were counted and categorized.

Example 31

Effect of Antisense to Integrin α4 on Peripheralization of Hemopoietic Progenitor Cells Mobilization (peripheralization) of hemopoietic progenitor cells from the bone marrow into the blood circulation is clinically useful in stem cell transplantation. A murine model has been established to evaluate the effects of drug compounds on this process (and its reverse, selective lodgement or homing of transplanted stem cells to the recipient's bone marrow)(Papayannopoulou et al., *Proc. Nat. Acad. Sci.* 1995, 92, 9647–9651). Briefly, pathogen-free mice 3–6 months old are used and are housed in a filtered-air-flow housing unit for the duration of the experiment. Mice used as primary or secondary recipients in the homing assay are exposed to 1150-cGy irradiation delivered from a Cs source.

Single cell suspensions are prepared from peripheral blood, bone marrow and spleen. Peripheral blood is obtained in preservative-free heparin by cardiac puncture and nucleated cells are recovered using $NH_4Cl$ hemolytic buffer. Bone marrow cells are obtained by flushing femoral marrow, under sterile conditions, with Iscove's modified Dulbecco's medium (IMDM) containing 10% v/v fetal bovine serum and streptomycin (50 ug/ml) and penicillin (50 U/ml). Splenic cell suspensions are obtained by lengthwise dissection of the spleen with a scalpel and scraping of cellular contents from the capsule, followed by vigorous pipetting. All cell suspensions are washed twice in IMDM with 10% fetal bovine serum. Cell counts are obtained using a hemocytometer.

Culture colony-forming unit (CFU-C) and spleen colony-forming unit (CFU-S) assays are performed as described in Papayannopoulou et al.,(*Proc. Natl. Acad. Sci.* 1995, 92, 9647–9651).

To assess hemopoietic progenitor mobilization in normal animals, the oligonucleotide is administered by daily IV injection (at dose ranges from 1 mg/kg to 5 mg/kg) for three days. Mice are sacrificed on the fourth day. Nucleated cells present in 0.25–0.5 ml of peripheral blood are plated in clonogenic progenitor cultures to assess CFU-C content, as described in Papayannopoulou et al.,(*Proc. Natl. Acad. Sci.* 1995, 92,9647–9651).

What is claimed is:

1. An antisense compound 8 to 30 nucleotides in length targeted to a nucleic acid molecule encoding human integrin α4, wherein said antisense compound inhibits the expression of human integrin α4.

2. The antisense compound of claim 1 which is an antisense oligonucleotide.

3. The antisense compound of claim 2 wherein the antisense oligonucleotide comprises SEQ ID NO: 13, 15, 35, 37, 39 or 46.

4. The antisense compound of claim 2 which comprises at least one modified internucleoside linkage.

5. The antisense compound of claim 4 wherein the modified internucleoside linkage is a phosphorothioate linkage.

6. The antisense compound of claim 2 which comprises at least one modified sugar moiety.

7. The antisense compound of claim 6 wherein the modified sugar moiety is a 2'-O-methoxyethyl sugar moiety.

8. The antisense compound of claim 2 which comprises at least one modified nucleobase.

9. The antisense compound of claim 8 wherein the modified nucleobase is a 5-methylcytosine.

10. The antisense compound of claim 1 which is a chimeric oligonucleotide.

11. A method of inhibiting the expression of human integrin α4 in human cells or tissues comprising contacting said cells or tissues in vitro with the antisense compound of claim 1 so that expression of human integrin α4 is inhibited.

* * * * *

SEQUENCE LISTING

```
<160> NUMBER OF SEQ ID NOS: 60

<210> SEQ ID NO 1
<211> LENGTH: 3567
<212> TYPE: DNA
<213> ORGANISM: Homo sapiens
<220> FEATURE:
<221> NAME/KEY: CDS
<222> LOCATION: (411)..(3527)
<300> PUBLICATION INFORMATION:
<308> DATABASE ACCESSION NUMBER: L12002 Genbank
<309> DATABASE ENTRY DATE: 1996-02-15

<400> SEQUENCE: 1
cgccatcccg cgctctgcgg actgggaggc ccgggccagg acgcgagtct gcgcagccga      60
ggttccccag cgccccctgc agccgcgcgt aggcagagac ggagcccggc cctgcgcctc     120
cgcaccacgc ccgggacccc acccagcggc ccgtacccgg agaagcagcg cgagcacccg     180
aagctcccgg ctcggcggca gaaacgggga gtggggccgg gcgagtgcgc ggcatcccag     240
gccggcccga acgtccgccc gcggtgggcc gacttcccct cctcttccct ctctccttcc     300
```

```
tttagccgc tggcgccgga cacgctgcgc ctcatctctt ggggcgttct tccccgttgg        360
ccaaccgtcg catcccgtgc aactttgggg tagtggccgc ttagtgttga atg ttc        416
                                                       Met Phe
                                                         1 ccc acc gag agc gca tgg ctt ggg aag cga ggc gcg aac ccg ggc ccc        464
Pro Thr Glu Ser Ala Trp Leu Gly Lys Arg Gly Ala Asn Pro Gly Pro
         5                  10                  15 gaa gcc gcc gtc cgg gag acg gtg atg ctg ttg ctg tgc ctg ggg gtc        512
Glu Ala Ala Val Arg Glu Thr Val Met Leu Leu Leu Cys Leu Gly Val
 20                  25                  30 ccg acc ggc cgc ccc tac aac gtg gac act gag agc gcg ctg ctt tac        560
Pro Thr Gly Arg Pro Tyr Asn Val Asp Thr Glu Ser Ala Leu Leu Tyr
 35                  40                  45                  50 cag ggc ccc cac aac acg ctg ttc ggc tac tcg gtc gtg ctg cac agc        608
Gln Gly Pro His Asn Thr Leu Phe Gly Tyr Ser Val Val Leu His Ser
                     55                  60                  65 cac ggg gcg aac cga tgg ctc cta gtg ggt gcg ccc act gcc aac tgg        656
His Gly Ala Asn Arg Trp Leu Leu Val Gly Ala Pro Thr Ala Asn Trp
                 70                  75                  80 ctc gcc aac gct tca gtg atc aat ccc ggg gcg att tac aga tgc agg        704
Leu Ala Asn Ala Ser Val Ile Asn Pro Gly Ala Ile Tyr Arg Cys Arg
             85                  90                  95 atc gga aag aat ccc ggc cag acg tgc gaa cag ctc cag ctg ggt agc        752
Ile Gly Lys Asn Pro Gly Gln Thr Cys Glu Gln Leu Gln Leu Gly Ser
        100                 105                 110 cct aat gga gaa cct tgt gga aag act tgt ttg gaa gag aga gac aat        800
Pro Asn Gly Glu Pro Cys Gly Lys Thr Cys Leu Glu Glu Arg Asp Asn
115                 120                 125                 130 cag tgg ttg ggg gtc aca ctt tcc aga cag cca gga gaa aat gga tcc        848
Gln Trp Leu Gly Val Thr Leu Ser Arg Gln Pro Gly Glu Asn Gly Ser
                135                 140                 145 atc gtg act tgt ggg cat aga tgg aaa aat ata ttt tac ata aag aat        896
Ile Val Thr Cys Gly His Arg Trp Lys Asn Ile Phe Tyr Ile Lys Asn
            150                 155                 160 gaa aat aag ctc ccc act ggt ggt tgc tat gga gtg ccc cct gat tta        944
Glu Asn Lys Leu Pro Thr Gly Gly Cys Tyr Gly Val Pro Pro Asp Leu
        165                 170                 175 cga aca gaa ctg agt aaa aga ata gct ccg tgt tat caa gat tat gtg        992
Arg Thr Glu Leu Ser Lys Arg Ile Ala Pro Cys Tyr Gln Asp Tyr Val
    180                 185                 190 aaa aaa ttt gga gaa aat ttt gca tca tgt caa gct gga ata tcc agt       1040
Lys Lys Phe Gly Glu Asn Phe Ala Ser Cys Gln Ala Gly Ile Ser Ser
195                 200                 205                 210 ttt tac aca aag gat tta att gtg atg ggg gcc cca gga tca tct tac       1088
Phe Tyr Thr Lys Asp Leu Ile Val Met Gly Ala Pro Gly Ser Ser Tyr
                215                 220                 225 tgg act ggc tct ctt ttt gtc tac aat ata act aca aat aaa tac aag       1136
Trp Thr Gly Ser Leu Phe Val Tyr Asn Ile Thr Thr Asn Lys Tyr Lys
            230                 235                 240 gct ttt tta gac aaa caa aat caa gta aaa ttt gga agt tat tta gga       1184
Ala Phe Leu Asp Lys Gln Asn Gln Val Lys Phe Gly Ser Tyr Leu Gly
        245                 250                 255 tat tca gtc gga gct ggt cat ttt cgg agc cag cat act acc gaa gta       1232
Tyr Ser Val Gly Ala Gly His Phe Arg Ser Gln His Thr Thr Glu Val
    260                 265                 270 gtc gga gga gct cct caa cat gag cag att ggt aag gca tat ata ttc       1280
Val Gly Gly Ala Pro Gln His Glu Gln Ile Gly Lys Ala Tyr Ile Phe
275                 280                 285                 290 agc att gat gaa aaa gaa cta aat atc tta cat gaa atg aaa ggt aaa       1328
```

```
                Ser Ile Asp Glu Lys Glu Leu Asn Ile Leu His Glu Met Lys Gly Lys
                            295                 300                 305 aag ctt gga tcg tac ttt gga gct tct gtc tgt gct gtg gac ctc aat        1376
Lys Leu Gly Ser Tyr Phe Gly Ala Ser Val Cys Ala Val Asp Leu Asn
            310                 315                 320 gca gat ggc ttc tca gat ctg ctc gtg gga gca ccc atg cag agc acc        1424
Ala Asp Gly Phe Ser Asp Leu Leu Val Gly Ala Pro Met Gln Ser Thr
        325                 330                 335 atc aga gag gaa gga aga gtg ttt gtg tac atc aac tct ggc tcg gga        1472
Ile Arg Glu Glu Gly Arg Val Phe Val Tyr Ile Asn Ser Gly Ser Gly
340                 345                 350 gca gta atg aat gca atg gaa aca aac ctc gtt gga agt gac aaa tat        1520
Ala Val Met Asn Ala Met Glu Thr Asn Leu Val Gly Ser Asp Lys Tyr
355                 360                 365                 370 gct gca aga ttt ggg gaa tct ata gtt aat ctt ggc gac att gac aat        1568
Ala Ala Arg Phe Gly Glu Ser Ile Val Asn Leu Gly Asp Ile Asp Asn
                375                 380                 385 gat ggc ttt gaa gat gtt gct atc gga gct cca caa gaa gat gac ttg        1616
Asp Gly Phe Glu Asp Val Ala Ile Gly Ala Pro Gln Glu Asp Asp Leu
            390                 395                 400 caa ggt gct att tat att tac aat ggc cgt gca gat ggg atc tcg tca        1664
Gln Gly Ala Ile Tyr Ile Tyr Asn Gly Arg Ala Asp Gly Ile Ser Ser
        405                 410                 415 acc ttc tca cag aga att gaa gga ctt cag atc agc aaa tcg tta agt        1712
Thr Phe Ser Gln Arg Ile Glu Gly Leu Gln Ile Ser Lys Ser Leu Ser
    420                 425                 430 atg ttt gga cag tct ata tca gga caa att gat gca gat aat aat ggc        1760
Met Phe Gly Gln Ser Ile Ser Gly Gln Ile Asp Ala Asp Asn Asn Gly
435                 440                 445                 450 tat gta gat gta gca gtt ggt gct ttt cgg tct gat tct gct gtc ttg        1808
Tyr Val Asp Val Ala Val Gly Ala Phe Arg Ser Asp Ser Ala Val Leu
                455                 460                 465 cta agg aca aga cct gta gta att gtt gac gct tct tta agc cac cct        1856
Leu Arg Thr Arg Pro Val Val Ile Val Asp Ala Ser Leu Ser His Pro
            470                 475                 480 gag tca gta aat aga acg aaa ttt gac tgt gtt gaa aat gga tgg cct        1904
Glu Ser Val Asn Arg Thr Lys Phe Asp Cys Val Glu Asn Gly Trp Pro
        485                 490                 495 tct gtg tgc ata gat cta aca ctt tgt ttc tca tat aag ggc aag gaa        1952
Ser Val Cys Ile Asp Leu Thr Leu Cys Phe Ser Tyr Lys Gly Lys Glu
    500                 505                 510 gtt cca ggt tac att gtt ttg ttt tat aac atg agt ttg gat gtg aac        2000
Val Pro Gly Tyr Ile Val Leu Phe Tyr Asn Met Ser Leu Asp Val Asn
515                 520                 525                 530 aga aag gca gag tct cca cca aga ttc tat ttc tct tct aat gga act        2048
Arg Lys Ala Glu Ser Pro Pro Arg Phe Tyr Phe Ser Ser Asn Gly Thr
                535                 540                 545 tct gac gtg att aca gga agc ata cag gtg tcc agc aga gaa gct aac        2096
Ser Asp Val Ile Thr Gly Ser Ile Gln Val Ser Ser Arg Glu Ala Asn
            550                 555                 560 tgt aga aca cat caa gca ttt atg cgg aaa gat gtg cgg gac atc ctc        2144
Cys Arg Thr His Gln Ala Phe Met Arg Lys Asp Val Arg Asp Ile Leu
        565                 570                 575 acc cca att cag att gaa gct gct tac cac ctt ggt cct cat gtc atc        2192
Thr Pro Ile Gln Ile Glu Ala Ala Tyr His Leu Gly Pro His Val Ile
    580                 585                 590 agt aaa cga agt aca gag gaa ttc cca cca ctt cag cca att ctt cag        2240
Ser Lys Arg Ser Thr Glu Glu Phe Pro Pro Leu Gln Pro Ile Leu Gln
595                 600                 605                 610 cag aag aaa gaa aaa gac ata atg aaa aaa aca ata aac ttt gca agg        2288
```

|     |     |     |     |     |     |     |     |     |     |     |     |     |     |     |     |
| --- | --- | --- | --- | --- | --- | --- | --- | --- | --- | --- | --- | --- | --- | --- | --- |
| Gln | Lys | Lys | Glu | Lys | Asp | Ile | Met | Lys | Lys | Thr | Ile | Asn | Phe | Ala | Arg |
|     |     |     |     | 615 |     |     |     | 620 |     |     |     | 625 |     |     |     |

| ttt | tgt | gcc | cat | gaa | aat | tgt | tct | gct | gat | tta | cag | gtt | tct | gca | aag | 2336 |
| --- | --- | --- | --- | --- | --- | --- | --- | --- | --- | --- | --- | --- | --- | --- | --- | --- |
| Phe | Cys | Ala | His | Glu | Asn | Cys | Ser | Ala | Asp | Leu | Gln | Val | Ser | Ala | Lys |     |
|     |     |     | 630 |     |     |     | 635 |     |     |     | 640 |     |     |     |     |     |

| att | ggg | ttt | ttg | aag | ccc | cat | gaa | aat | aaa | aca | tat | ctt | gct | gtt | ggg | 2384 |
| --- | --- | --- | --- | --- | --- | --- | --- | --- | --- | --- | --- | --- | --- | --- | --- | --- |
| Ile | Gly | Phe | Leu | Lys | Pro | His | Glu | Asn | Lys | Thr | Tyr | Leu | Ala | Val | Gly |     |
|     |     |     |     | 645 |     |     |     | 650 |     |     |     | 655 |     |     |     |     |

| agt | atg | aag | aca | ttg | atg | ttg | aat | gtg | tcc | ttg | ttt | aat | gct | gga | gat | 2432 |
| --- | --- | --- | --- | --- | --- | --- | --- | --- | --- | --- | --- | --- | --- | --- | --- | --- |
| Ser | Met | Lys | Thr | Leu | Met | Leu | Asn | Val | Ser | Leu | Phe | Asn | Ala | Gly | Asp |     |
|     |     |     | 660 |     |     |     | 665 |     |     |     | 670 |     |     |     |     |     |

| gat | gca | tat | gaa | acg | act | cta | cat | gtc | aaa | cta | ccc | gtg | ggt | ctt | tat | 2480 |
| --- | --- | --- | --- | --- | --- | --- | --- | --- | --- | --- | --- | --- | --- | --- | --- | --- |
| Asp | Ala | Tyr | Glu | Thr | Thr | Leu | His | Val | Lys | Leu | Pro | Val | Gly | Leu | Tyr |     |
| 675 |     |     |     | 680 |     |     |     | 685 |     |     |     | 690 |     |     |     |     |

| ttc | att | aag | att | tta | gag | ctg | gaa | gag | aag | caa | ata | aac | tgt | gaa | gtc | 2528 |
| --- | --- | --- | --- | --- | --- | --- | --- | --- | --- | --- | --- | --- | --- | --- | --- | --- |
| Phe | Ile | Lys | Ile | Leu | Glu | Leu | Glu | Glu | Lys | Gln | Ile | Asn | Cys | Glu | Val |     |
|     |     |     |     | 695 |     |     |     | 700 |     |     |     | 705 |     |     |     |     |

| aca | gat | aac | tct | ggc | gtg | gta | caa | ctt | gac | tgc | agt | att | ggc | tat | ata | 2576 |
| --- | --- | --- | --- | --- | --- | --- | --- | --- | --- | --- | --- | --- | --- | --- | --- | --- |
| Thr | Asp | Asn | Ser | Gly | Val | Val | Gln | Leu | Asp | Cys | Ser | Ile | Gly | Tyr | Ile |     |
|     |     |     | 710 |     |     |     | 715 |     |     |     | 720 |     |     |     |     |     |

| tat | gta | gat | cat | ctc | tca | agg | ata | gat | att | agc | ttt | ctc | ctg | gat | gtg | 2624 |
| --- | --- | --- | --- | --- | --- | --- | --- | --- | --- | --- | --- | --- | --- | --- | --- | --- |
| Tyr | Val | Asp | His | Leu | Ser | Arg | Ile | Asp | Ile | Ser | Phe | Leu | Leu | Asp | Val |     |
|     |     | 725 |     |     |     | 730 |     |     |     | 735 |     |     |     |     |     |     |

| agc | tca | ctc | agc | aga | gcg | gaa | gag | gac | ctc | agt | atc | aca | gtg | cat | gct | 2672 |
| --- | --- | --- | --- | --- | --- | --- | --- | --- | --- | --- | --- | --- | --- | --- | --- | --- |
| Ser | Ser | Leu | Ser | Arg | Ala | Glu | Glu | Asp | Leu | Ser | Ile | Thr | Val | His | Ala |     |
|     | 740 |     |     |     | 745 |     |     |     | 750 |     |     |     |     |     |     |     |

| acc | tgt | gaa | aat | gaa | gag | gaa | atg | gac | aat | cta | aag | cac | agc | aga | gtg | 2720 |
| --- | --- | --- | --- | --- | --- | --- | --- | --- | --- | --- | --- | --- | --- | --- | --- | --- |
| Thr | Cys | Glu | Asn | Glu | Glu | Glu | Met | Asp | Asn | Leu | Lys | His | Ser | Arg | Val |     |
| 755 |     |     |     | 760 |     |     |     | 765 |     |     |     | 770 |     |     |     |     |

| act | gta | gca | ata | cct | tta | aaa | tat | gag | gtt | aag | ctg | act | gtt | cat | ggg | 2768 |
| --- | --- | --- | --- | --- | --- | --- | --- | --- | --- | --- | --- | --- | --- | --- | --- | --- |
| Thr | Val | Ala | Ile | Pro | Leu | Lys | Tyr | Glu | Val | Lys | Leu | Thr | Val | His | Gly |     |
|     |     |     |     | 775 |     |     |     | 780 |     |     |     | 785 |     |     |     |     |

| ttt | gta | aac | cca | act | tca | ttt | gtg | tat | gga | tca | aat | gat | gaa | aat | gag | 2816 |
| --- | --- | --- | --- | --- | --- | --- | --- | --- | --- | --- | --- | --- | --- | --- | --- | --- |
| Phe | Val | Asn | Pro | Thr | Ser | Phe | Val | Tyr | Gly | Ser | Asn | Asp | Glu | Asn | Glu |     |
|     |     |     | 790 |     |     |     | 795 |     |     |     | 800 |     |     |     |     |     |

| cct | gaa | acg | tgc | atg | gtg | gag | aaa | atg | aac | tta | act | ttc | cat | gtt | atc | 2864 |
| --- | --- | --- | --- | --- | --- | --- | --- | --- | --- | --- | --- | --- | --- | --- | --- | --- |
| Pro | Glu | Thr | Cys | Met | Val | Glu | Lys | Met | Asn | Leu | Thr | Phe | His | Val | Ile |     |
|     | 805 |     |     |     | 810 |     |     |     | 815 |     |     |     |     |     |     |     |

| aac | act | ggc | aat | agt | atg | gct | ccc | aat | gtt | agt | gtg | gaa | ata | atg | gta | 2912 |
| --- | --- | --- | --- | --- | --- | --- | --- | --- | --- | --- | --- | --- | --- | --- | --- | --- |
| Asn | Thr | Gly | Asn | Ser | Met | Ala | Pro | Asn | Val | Ser | Val | Glu | Ile | Met | Val |     |
|     | 820 |     |     |     | 825 |     |     |     | 830 |     |     |     |     |     |     |     |

| cca | aat | tct | ttt | agc | ccc | caa | act | gat | aag | ctg | ttc | aac | att | ttg | gat | 2960 |
| --- | --- | --- | --- | --- | --- | --- | --- | --- | --- | --- | --- | --- | --- | --- | --- | --- |
| Pro | Asn | Ser | Phe | Ser | Pro | Gln | Thr | Asp | Lys | Leu | Phe | Asn | Ile | Leu | Asp |     |
| 835 |     |     |     | 840 |     |     |     | 845 |     |     |     |     |     |     | 850 |     |

| gtc | cag | act | act | act | gga | gaa | tgc | cac | ttt | gaa | aat | tat | caa | aga | gtg | 3008 |
| --- | --- | --- | --- | --- | --- | --- | --- | --- | --- | --- | --- | --- | --- | --- | --- | --- |
| Val | Gln | Thr | Thr | Thr | Gly | Glu | Cys | His | Phe | Glu | Asn | Tyr | Gln | Arg | Val |     |
|     |     |     |     | 855 |     |     |     | 860 |     |     |     | 865 |     |     |     |     |

| tgt | gca | tta | gag | cag | caa | aag | agt | gca | atg | cag | acc | ttg | aaa | ggc | ata | 3056 |
| --- | --- | --- | --- | --- | --- | --- | --- | --- | --- | --- | --- | --- | --- | --- | --- | --- |
| Cys | Ala | Leu | Glu | Gln | Gln | Lys | Ser | Ala | Met | Gln | Thr | Leu | Lys | Gly | Ile |     |
|     |     |     | 870 |     |     |     | 875 |     |     |     | 880 |     |     |     |     |     |

| gtc | cag | ttc | ttg | tcc | aag | act | gat | aag | agg | cta | ttg | tac | tgc | ata | aaa | 3104 |
| --- | --- | --- | --- | --- | --- | --- | --- | --- | --- | --- | --- | --- | --- | --- | --- | --- |
| Val | Gln | Phe | Leu | Ser | Lys | Thr | Asp | Lys | Arg | Leu | Leu | Tyr | Cys | Ile | Lys |     |
|     |     | 885 |     |     |     | 890 |     |     |     | 895 |     |     |     |     |     |     |

| gct | gat | cca | cat | tgt | tta | aat | ttc | ttg | tgt | aat | ttt | ggg | aaa | atg | gaa | 3152 |
| --- | --- | --- | --- | --- | --- | --- | --- | --- | --- | --- | --- | --- | --- | --- | --- | --- |
| Ala | Asp | Pro | His | Cys | Leu | Asn | Phe | Leu | Cys | Asn | Phe | Gly | Lys | Met | Glu |     |
|     | 900 |     |     |     | 905 |     |     |     | 910 |     |     |     |     |     |     |     |

| agt | gga | aaa | gaa | gcc | agt | gtt | cat | atc | caa | ctg | gaa | ggc | cgg | cca | tcc | 3200 |
| --- | --- | --- | --- | --- | --- | --- | --- | --- | --- | --- | --- | --- | --- | --- | --- | --- |
| Ser | Gly | Lys | Glu | Ala | Ser | Val | His | Ile | Gln | Leu | Glu | Gly | Arg | Pro | Ser |     |
| 915 |     |     |     | 920 |     |     |     | 925 |     |     |     | 930 |     |     |     |     |

| att | tta | gaa | atg | gat | gag | act | tca | gca | ctc | aag | ttt | gaa | ata | aga | gca | 3248 |
| --- | --- | --- | --- | --- | --- | --- | --- | --- | --- | --- | --- | --- | --- | --- | --- | --- |

```
Ile Leu Glu Met Asp Glu Thr Ser Ala Leu Lys Phe Glu Ile Arg Ala
                935                 940                 945 aca ggt ttt cca gag cca aat cca aga gta att gaa cta aac aag gat    3296
Thr Gly Phe Pro Glu Pro Asn Pro Arg Val Ile Glu Leu Asn Lys Asp
        950                 955                 960 gag aat gtt gcg cat gtt cta ctg gaa gga cta cat cat caa aga ccc    3344
Glu Asn Val Ala His Val Leu Leu Glu Gly Leu His His Gln Arg Pro
    965                 970                 975 aaa cgt tat ttc acc ata gtg att att tca agt agc ttg cta ctt gga    3392
Lys Arg Tyr Phe Thr Ile Val Ile Ile Ser Ser Ser Leu Leu Leu Gly
        980                 985                 990 ctt att gta ctt ctg ttg atc tca tat gtt atg tgg aag gct ggc ttc    3440
Leu Ile Val Leu Leu Leu Ile Ser Tyr Val Met Trp Lys Ala Gly Phe
995                 1000                1005                1010 ttt aaa aga caa tac aaa tct atc cta caa gaa gaa aac aga aga gac    3488
Phe Lys Arg Gln Tyr Lys Ser Ile Leu Gln Glu Glu Asn Arg Arg Asp
            1015                1020                1025 agt tgg agt tat atc aac agt aaa agc aat gat gat taa ggacttcttt    3537
Ser Trp Ser Tyr Ile Asn Ser Lys Ser Asn Asp Asp
        1030                1035 caaattgaga gaatggaaaa cagcccgccc                                   3567

<210> SEQ ID NO 2
<211> LENGTH: 18
<212> TYPE: DNA
<213> ORGANISM: Artificial Sequence
<220> FEATURE:
<223> OTHER INFORMATION: antisense sequence

<400> SEQUENCE: 2
ctccgtctct gcctacgc                                                18

<210> SEQ ID NO 3
<211> LENGTH: 18
<212> TYPE: DNA
<213> ORGANISM: Artificial Sequence
<220> FEATURE:
<223> OTHER INFORMATION: antisense sequence

<400> SEQUENCE: 3
cgggtgctcg cgctgctt                                                18

<210> SEQ ID NO 4
<211> LENGTH: 18
<212> TYPE: DNA
<213> ORGANISM: Artificial Sequence
<220> FEATURE:
<223> OTHER INFORMATION: antisense sequence

<400> SEQUENCE: 4
cctgggatgc cgcgcact                                                18

<210> SEQ ID NO 5
<211> LENGTH: 18
<212> TYPE: DNA
<213> ORGANISM: Artificial Sequence
<220> FEATURE:
<223> OTHER INFORMATION: antisense sequence

<400> SEQUENCE: 5
atgaggcgca gcgtgtcc                                                18

<210> SEQ ID NO 6
<211> LENGTH: 18
```

```
<212> TYPE: DNA
<213> ORGANISM: Artificial Sequence
<220> FEATURE:
<223> OTHER INFORMATION: antisense sequence

<400> SEQUENCE: 6
caaagttgca cgggatgc                                              18

<210> SEQ ID NO 7
<211> LENGTH: 18
<212> TYPE: DNA
<213> ORGANISM: Artificial Sequence
<220> FEATURE:
<223> OTHER INFORMATION: antisense sequence

<400> SEQUENCE: 7
ggaacattca acactaag                                              18

<210> SEQ ID NO 8
<211> LENGTH: 18
<212> TYPE: DNA
<213> ORGANISM: Artificial Sequence
<220> FEATURE:
<223> OTHER INFORMATION: antisense sequence

<400> SEQUENCE: 8
cccgggttcg cgcctcgc                                              18

<210> SEQ ID NO 9
<211> LENGTH: 18
<212> TYPE: DNA
<213> ORGANISM: Artificial Sequence
<220> FEATURE:
<223> OTHER INFORMATION: antisense sequence

<400> SEQUENCE: 9
gcgcgctctc agtgtcca                                              18

<210> SEQ ID NO 10
<211> LENGTH: 18
<212> TYPE: DNA
<213> ORGANISM: Artificial Sequence
<220> FEATURE:
<223> OTHER INFORMATION: antisense sequence

<400> SEQUENCE: 10
gtggctgtgc agcacgac                                              18

<210> SEQ ID NO 11
<211> LENGTH: 18
<212> TYPE: DNA
<213> ORGANISM: Artificial Sequence
<220> FEATURE:
<223> OTHER INFORMATION: antisense sequence

<400> SEQUENCE: 11
actgaagcgt tggcgagc                                              18

<210> SEQ ID NO 12
<211> LENGTH: 18
<212> TYPE: DNA
<213> ORGANISM: Artificial Sequence
<220> FEATURE:
<223> OTHER INFORMATION: antisense sequence

<400> SEQUENCE: 12
gcacgtctgg ccgggatt                                              18
```

```
<210> SEQ ID NO 13
<211> LENGTH: 18
<212> TYPE: DNA
<213> ORGANISM: Artificial Sequence
<220> FEATURE:
<223> OTHER INFORMATION: antisense sequence

<400> SEQUENCE: 13
ccactgattg tctctctc                                                       18

<210> SEQ ID NO 14
<211> LENGTH: 18
<212> TYPE: DNA
<213> ORGANISM: Artificial Sequence
<220> FEATURE:
<223> OTHER INFORMATION: antisense sequence

<400> SEQUENCE: 14
ggatccattt tctcctgg                                                       18

<210> SEQ ID NO 15
<211> LENGTH: 18
<212> TYPE: DNA
<213> ORGANISM: Artificial Sequence
<220> FEATURE:
<223> OTHER INFORMATION: antisense sequence

<400> SEQUENCE: 15
gcttattttc attcttta                                                       18

<210> SEQ ID NO 16
<211> LENGTH: 18
<212> TYPE: DNA
<213> ORGANISM: Artificial Sequence
<220> FEATURE:
<223> OTHER INFORMATION: antisense sequence

<400> SEQUENCE: 16
ttcttttact cagttctg                                                       18

<210> SEQ ID NO 17
<211> LENGTH: 18
<212> TYPE: DNA
<213> ORGANISM: Artificial Sequence
<220> FEATURE:
<223> OTHER INFORMATION: antisense sequence

<400> SEQUENCE: 17
tcacataatc ttgataac                                                       18

<210> SEQ ID NO 18
<211> LENGTH: 18
<212> TYPE: DNA
<213> ORGANISM: Artificial Sequence
<220> FEATURE:
<223> OTHER INFORMATION: antisense sequence

<400> SEQUENCE: 18
cccatcacaa ttaaatcc                                                       18

<210> SEQ ID NO 19
<211> LENGTH: 18
<212> TYPE: DNA
<213> ORGANISM: Artificial Sequence
<220> FEATURE:
<223> OTHER INFORMATION: antisense sequence
```

```
<400> SEQUENCE: 19
ttatttgtag ttatattg                                              18

<210> SEQ ID NO 20
<211> LENGTH: 18
<212> TYPE: DNA
<213> ORGANISM: Artificial Sequence
<220> FEATURE:
<223> OTHER INFORMATION: antisense sequence

<400> SEQUENCE: 20
cctaaataac ttccaaat                                              18

<210> SEQ ID NO 21
<211> LENGTH: 18
<212> TYPE: DNA
<213> ORGANISM: Artificial Sequence
<220> FEATURE:
<223> OTHER INFORMATION: antisense sequence

<400> SEQUENCE: 21
gaaaatgacc agctccga                                              18

<210> SEQ ID NO 22
<211> LENGTH: 18
<212> TYPE: DNA
<213> ORGANISM: Artificial Sequence
<220> FEATURE:
<223> OTHER INFORMATION: antisense sequence

<400> SEQUENCE: 22
tttcatgtaa gatattta                                              18

<210> SEQ ID NO 23
<211> LENGTH: 18
<212> TYPE: DNA
<213> ORGANISM: Artificial Sequence
<220> FEATURE:
<223> OTHER INFORMATION: antisense sequence

<400> SEQUENCE: 23
ccacagcaca gacagaag                                              18

<210> SEQ ID NO 24
<211> LENGTH: 18
<212> TYPE: DNA
<213> ORGANISM: Artificial Sequence
<220> FEATURE:
<223> OTHER INFORMATION: antisense sequence

<400> SEQUENCE: 24
tggtgctctg catgggtg                                              18

<210> SEQ ID NO 25
<211> LENGTH: 18
<212> TYPE: DNA
<213> ORGANISM: Artificial Sequence
<220> FEATURE:
<223> OTHER INFORMATION: antisense sequence

<400> SEQUENCE: 25
tacacaaaca ctcttcct                                              18

<210> SEQ ID NO 26
<211> LENGTH: 18
```

```
<212> TYPE: DNA
<213> ORGANISM: Artificial Sequence
<220> FEATURE:
<223> OTHER INFORMATION: antisense sequence

<400> SEQUENCE: 26
tttgtttcca ttgcattc                                                    18

<210> SEQ ID NO 27
<211> LENGTH: 18
<212> TYPE: DNA
<213> ORGANISM: Artificial Sequence
<220> FEATURE:
<223> OTHER INFORMATION: antisense sequence

<400> SEQUENCE: 27
tgcagcatat ttgtcact                                                    18

<210> SEQ ID NO 28
<211> LENGTH: 18
<212> TYPE: DNA
<213> ORGANISM: Artificial Sequence
<220> FEATURE:
<223> OTHER INFORMATION: antisense sequence

<400> SEQUENCE: 28
ttgtcaatgt cgccaaga                                                    18

<210> SEQ ID NO 29
<211> LENGTH: 18
<212> TYPE: DNA
<213> ORGANISM: Artificial Sequence
<220> FEATURE:
<223> OTHER INFORMATION: antisense sequence

<400> SEQUENCE: 29
tcatcttctt gtggagct                                                    18

<210> SEQ ID NO 30
<211> LENGTH: 18
<212> TYPE: DNA
<213> ORGANISM: Artificial Sequence
<220> FEATURE:
<223> OTHER INFORMATION: antisense sequence

<400> SEQUENCE: 30
ccatctgcac ggccattg                                                    18

<210> SEQ ID NO 31
<211> LENGTH: 18
<212> TYPE: DNA
<213> ORGANISM: Artificial Sequence
<220> FEATURE:
<223> OTHER INFORMATION: antisense sequence

<400> SEQUENCE: 31
gtccaaacat acttaacg                                                    18

<210> SEQ ID NO 32
<211> LENGTH: 18
<212> TYPE: DNA
<213> ORGANISM: Artificial Sequence
<220> FEATURE:
<223> OTHER INFORMATION: antisense sequence

<400> SEQUENCE: 32
tatctgcatc aatttgtc                                                    18
```

```
<210> SEQ ID NO 33
<211> LENGTH: 18
<212> TYPE: DNA
<213> ORGANISM: Artificial Sequence
<220> FEATURE:
<223> OTHER INFORMATION: antisense sequence

<400> SEQUENCE: 33
accgaaaagc accaactg                                                   18

<210> SEQ ID NO 34
<211> LENGTH: 18
<212> TYPE: DNA
<213> ORGANISM: Artificial Sequence
<220> FEATURE:
<223> OTHER INFORMATION: antisense sequence

<400> SEQUENCE: 34
cttgtcctta gcaagaca                                                   18

<210> SEQ ID NO 35
<211> LENGTH: 18
<212> TYPE: DNA
<213> ORGANISM: Artificial Sequence
<220> FEATURE:
<223> OTHER INFORMATION: antisense sequence

<400> SEQUENCE: 35
tcagggtggc ttaaagaa                                                   18

<210> SEQ ID NO 36
<211> LENGTH: 18
<212> TYPE: DNA
<213> ORGANISM: Artificial Sequence
<220> FEATURE:
<223> OTHER INFORMATION: antisense sequence

<400> SEQUENCE: 36
atccattttc aacacagt                                                   18

<210> SEQ ID NO 37
<211> LENGTH: 18
<212> TYPE: DNA
<213> ORGANISM: Artificial Sequence
<220> FEATURE:
<223> OTHER INFORMATION: antisense sequence

<400> SEQUENCE: 37
gcccttatat gagaaaca                                                   18

<210> SEQ ID NO 38
<211> LENGTH: 18
<212> TYPE: DNA
<213> ORGANISM: Artificial Sequence
<220> FEATURE:
<223> OTHER INFORMATION: antisense sequence

<400> SEQUENCE: 38
caatttgaaa gaagtcct                                                   18

<210> SEQ ID NO 39
<211> LENGTH: 18
<212> TYPE: DNA
<213> ORGANISM: Artificial Sequence
<220> FEATURE:
<223> OTHER INFORMATION: antisense sequence
```

```
<400> SEQUENCE: 39
tccattctct caatttga                                                    18

<210> SEQ ID NO 40
<211> LENGTH: 18
<212> TYPE: DNA
<213> ORGANISM: Artificial Sequence
<220> FEATURE:
<223> OTHER INFORMATION: antisense sequence

<400> SEQUENCE: 40
ggcgggctgt tttccatt                                                    18

<210> SEQ ID NO 41
<211> LENGTH: 1300
<212> TYPE: DNA
<213> ORGANISM: Homo sapiens
<220> FEATURE:
<221> NAME/KEY: CDS
<222> LOCATION: (1152)..(1283)
<300> PUBLICATION INFORMATION:
<308> DATABASE ACCESSION NUMBER: M62841 genbank
<309> DATABASE ENTRY DATE: 1994-10-30

<400> SEQUENCE: 41
ggcagggcac acctggattg cattagaatg agactcacta cccagttcag gtgtgttgcg       60
ttgtgggtct ccggcacatt tcagaggctg attaggaccc tgaccccaca ctggggttta      120 caccctaaa agcaggtgtg tcccgtggca actgagtggg tgcgtgaaaa ggggggatca       180
tcaattacca gctggagcaa tcgaatcggt taaatgtgaa tcaagtcaca gtgcttcctt      240
aacccaacct ctctgttggg gtcagccaca gcctaaaccg cctgccgttc agcctgagag      300
gctgctgcta gcctgctcac gcatgcagcc cgggctgcag aggaagtgtg gggaggaagg      360
aagtgggtat agaagggtgc tgagatgtgg gtcttgaaga gaatagccat aacgtctttg      420
tcactaaaat gttccccagg ggccttcggc gagtcttttt gtttggtttt ttgtttttaa      480
tctgtggctc ttgataaattt atctagtggt tgcctacacc tgaaaaacaa gacacagtgt     540
ttaactatca cgaaagaac tggacggctc cccgccgcag tcccactccc cgagtttgtg      600
gctggcattt gggccacgcc gggctgggcg gctcacagcg aggggcgcgc agtttggggt      660
cacacagctc cgcttctagg ccccaaccac cgttaaaagg ggaagcccgt gccccatcag     720
gtccgctctt gctgagccca gagccatccc gcgctctgcg ggctgggagg cccgggccag     780
acgcgagtcc tgcgcagccg aggttcccca gcgcccctg cagccgcgcg taggcagaga     840
cggagcccgg ccctgcgcct ccgcaccacg cccgggaccc cacccagcgg cccgtacccg     900
gagaagcagc gcgagcaccc gaagctcccg gctcggcggc agaaaccggg agtggggccg     960
ggcgagtgcg cggcatccca ggccggcccg aacgtccgcc cgcggtgggc cgacttcccc   1020
tcctcttccc tctctccttc ctttagcccg ctggcgccgg acacgctgcg cctcatctct   1080
tggggcgttc ttccccgttg gccaaccgtc gcatccgtg caactttggg gtagtggccg    1140
cttagtgttg a atg ttc ccc acc gag agc gca tgg ctt ggg aag cga ggc   1190
              Met Phe Pro Thr Glu Ser Ala Trp Leu Gly Lys Arg Gly
               1               5                  10 gcg aac ccg ggc ccc gaa gcc gcc gtc cgg gag ggc ccc cac aac acg     1238
Ala Asn Pro Gly Pro Glu Ala Ala Val Arg Glu Gly Pro His Asn Thr
 15                  20                  25 ctg ttc ggc tac tcg gtc gtg ctg cac agc cac ggg gcg aac cga         1283
Leu Phe Gly Tyr Ser Val Val Leu His Ser His Gly Ala Asn Arg
 30                  35                  40
```

```
tggtgagtag agttgga                                                1300

<210> SEQ ID NO 42
<211> LENGTH: 20
<212> TYPE: DNA
<213> ORGANISM: Artificial Sequence
<220> FEATURE:
<223> OTHER INFORMATION: antisense sequence

<400> SEQUENCE: 42
tttagtgaca aagacgttat                                               20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
gaaggcccct ggggaacatt                                               20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

<400> SEQUENCE: 44
agacgttatg gctattctct                                               20

<210> SEQ ID NO 45
<211> LENGTH: 20
<212> TYPE: DNA
<213> ORGANISM: Artificial Sequence
<220> FEATURE:
<223> OTHER INFORMATION: antisense sequence

<400> SEQUENCE: 45
ttgcccttat atgagaaaca                                               20

<210> SEQ ID NO 46
<211> LENGTH: 20
<212> TYPE: DNA
<213> ORGANISM: Artificial Sequence
<220> FEATURE:
<223> OTHER INFORMATION: antisense sequence

<400> SEQUENCE: 46
cccaagccat gcgctctcgg                                               20

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
ccgcagccat gcgctcttgg                                               20

<210> SEQ ID NO 48
<211> LENGTH: 1771
<212> TYPE: DNA
<213> ORGANISM: Mus musculus
```

```
<220> FEATURE:
<221> NAME/KEY: CDS
<222> LOCATION: (1193)..(1387)
<220> FEATURE:
<221> NAME/KEY: CDS
<222> LOCATION: (1709)..(1771)
<300> PUBLICATION INFORMATION:
<308> DATABASE ACCESSION NUMBER: L20788 Genbank
<309> DATABASE ENTRY DATE: 1996-04-18

<400> SEQUENCE: 48
ccagcacttg cctcctgctc cagcgtgaaa agcagggaat ggaatatgga gtgtaagaca      60
taaattaaaa ataaaataaa attaaaaaaa aaaaaagaaa agcagcacac aaggagtatg     120
ttcagcagag gcccatctcc tggcttaggt gtgctgtgac tctgatctct ggtggctttt     180
tagaagcctg ttatgacctt gtcttaggct gtgtctacac atctggtggt aggtatgtcc     240
tggggtaact gagtgtgtac atggggacta gttatgaaga agtgagcaag gggtggagtc     300
tgctaagtga ggcaagtcac agaatttcct tagcttgcct gggttttctg tgttaggcta     360
ttgcctggct tgctcatgcg tatagactct atttaagagg aagtgtatag agaggaagga     420
agcctgcata aaaggctgca ggcctgggag ttttgaagag actagccata tacttttgtc     480
accaaatgct ccaataaggc tggggcggga gggggggggg cagcagtttt ggcttcttgc     540
aaactgtgta atttctgtat gctacacagc acataagtga cagaggaagt tctgaaggt      600 tctccacagt cttagttccc aaattattgg ccactgggac tggccctgga ggccagtcac     660
ttggtgaagt cccgcaaggc atcaagcctt agccaacttt caaaagggaa tcccctgatc     720
tgttttgtgt tcccccaagg gttattttttg ctgggcccca gaagccagag ccactgtgtg    780
tgatgtctgc cagggtgtga gtccatgcaa cctaggtccc ctagcgcccc ctacagctgc     840
tgcggggcgg ggatggggat cgggttgggg agagggaggc caggctgtga gccactgcac     900
cacacccagg accccaccca gatcctagga gcacccggcc cctggctccg ggccacagaa     960
acgggggcgt gggccagagc ctgaagcatc cctggccact acgatcgctc cgcctgtggc    1020
caccaattcc cctcctcttc tggcgtccct ctctccgccc ctgtcgcctg ccagcaccgg    1080
acacgctgct gcacttcatc tcttggggcg ctcttctctt tggccaaccg tcgcatcctg    1140
tgcaactctg gtcagtggcc gttttgtgtt gaatgttctc caccaagagc gc atg gct    1198
                                                           Met Ala
                                                             1 gcg gaa gcg agg tgc aga ccg agg tcc cga ggg atc gcc ctc cgg gaa     1246
Ala Glu Ala Arg Cys Arg Pro Arg Ser Arg Gly Ile Ala Leu Arg Glu
         5                  10                  15 gcg gtg atg ctg ttg ttg tac ttc ggg gtg cca acc ggg cac tcc tac     1294
Ala Val Met Leu Leu Leu Tyr Phe Gly Val Pro Thr Gly His Ser Tyr
     20                  25                  30 aac ctg gac ccg gag aat gca ctg ctg tac cag ggc ccc tcc ggc acg     1342
Asn Leu Asp Pro Glu Asn Ala Leu Leu Tyr Gln Gly Pro Ser Gly Thr
 35                  40                  45                  50 ctg ttt ggc tac tcg gtg gtg ctg cac agc cac ggg tcg aag cgc         1387
Leu Phe Gly Tyr Ser Val Val Leu His Ser His Gly Ser Lys Arg
                 55                  60                  65 tggtgagtgc gccctcccca agaggcatgt cacagcgcct ccgcctctgg gattccttgt    1447
atgaatcaaa ctttccgccc tcctgggagg tcagagaaag acctggcttc agccagctgc    1507
ctcactggag agccttggaa ctaacttatc ttgggatggc agcccccagg gtgctcctga    1567
gtcctgggtc tccagtcatg ggaagaggag gtgggtgcca cttcccttgc tgaccactgc    1627
acagctgtca caagccaaca cggggcagag tgggtgggca gactggttca cgtctgagcg    1687
```

```
aacttgcatg gttcttgctt t agg ctc atc gtg ggg gct ccc act gcc agc    1738
                      Trp Leu Ile Val Gly Ala Pro Thr Ala Ser
                                      70              75 tgg ctc tct aat gcc tca gtg gtc aat cct ggg                        1771
Trp Leu Ser Asn Ala Ser Val Val Asn Pro Gly
                80              85
```

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
cacgccccgt ttctgtggcc                                              20

<210> SEQ ID NO 50
<211> LENGTH: 20
<212> TYPE: DNA
<213> ORGANISM: Artificial Sequence
<220> FEATURE:
<223> OTHER INFORMATION: antisense sequence

<400> SEQUENCE: 50
ggatgcttca ggctctggcc                                              20

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
ggagcgatcg tagtggccag                                              20

<210> SEQ ID NO 52
<211> LENGTH: 20
<212> TYPE: DNA
<213> ORGANISM: Artificial Sequence
<220> FEATURE:
<223> OTHER INFORMATION: antisense sequence

<400> SEQUENCE: 52
ccggtgctgg caggcgacag                                              20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
gatgaagtgc agcagcgtgt                                              20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
ggccactgac cagagttgca                                              20

```
<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
cacctcgctt ccgcagccat                                               20

<210> SEQ ID NO 56
<211> LENGTH: 20
<212> TYPE: DNA
<213> ORGANISM: Artificial Sequence
<220> FEATURE:
<223> OTHER INFORMATION: control sequence

<400> SEQUENCE: 56
cggaccagta ccagggttac                                               20

<210> SEQ ID NO 57
<211> LENGTH: 20
<212> TYPE: DNA
<213> ORGANISM: Artificial Sequence
<220> FEATURE:
<223> OTHER INFORMATION: control sequence

<400> SEQUENCE: 57
gccgacaccc gttcgttcgg                                               20

<210> SEQ ID NO 58
<211> LENGTH: 20
<212> TYPE: DNA
<213> ORGANISM: Artificial Sequence
<220> FEATURE:
<223> OTHER INFORMATION: control sequence

<400> SEQUENCE: 58
acctcctcgc tcacgcgcta                                               20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
cgcttccgca gccatgcgct                                               20

<210> SEQ ID NO 60
<211> LENGTH: 13
<212> TYPE: PRT
<213> ORGANISM: Artificial Sequence
<220> FEATURE:
<223> OTHER INFORMATION: peptide sequence

<400> SEQUENCE: 60

His Ser Leu Gly Lys Trp Leu Gly His Pro Asp Lys Phe
1               5                   10
```